US010463270B2

(12) United States Patent
Leyde

(10) Patent No.: US 10,463,270 B2
(45) Date of Patent: Nov. 5, 2019

(54) LOW POWER DEVICE WITH CONTINGENT SCHEDULING

(71) Applicant: CYBERONICS, INC., Houston, TX (US)

(72) Inventor: Kent Leyde, Sammamish, WA (US)

(73) Assignee: LivaNova USA, Inc., Houston, TX (US)

( * ) Notice: Subject to any disclaimer, the term of this patent is extended or adjusted under 35 U.S.C. 154(b) by 538 days.

(21) Appl. No.: 14/954,250

(22) Filed: Nov. 30, 2015

(65) Prior Publication Data
US 2016/0081576 A1    Mar. 24, 2016

Related U.S. Application Data

(62) Division of application No. 11/616,788, filed on Dec. 27, 2006, now abandoned.

(51) Int. Cl.
| | |
|---|---|
| *A61B 5/0476* | (2006.01) |
| *A61B 5/00* | (2006.01) |
| *A61B 5/024* | (2006.01) |
| *G16H 40/63* | (2018.01) |

(52) U.S. Cl.
CPC .......... *A61B 5/0476* (2013.01); *A61B 5/0006* (2013.01); *A61B 5/024* (2013.01); *A61B 5/4094* (2013.01); *A61B 5/6814* (2013.01); *A61B 5/7264* (2013.01); *G16H 40/63* (2018.01); *A61B 2560/0209* (2013.01)

(58) Field of Classification Search
None
See application file for complete search history.

(56) References Cited

U.S. PATENT DOCUMENTS

| | | | |
|---|---|---|---|
| 4,566,464 A | 1/1986 | Piccone | |
| 4,679,144 A | 7/1987 | Cox et al. | |
| 5,047,930 A * | 9/1991 | Martens | ............... A61B 5/0476 128/920 |
| 5,311,876 A | 5/1994 | Olsen et al. | |
| 5,957,861 A | 9/1999 | Combs et al. | |
| 5,978,702 A | 11/1999 | Ward | |
| 5,978,710 A | 11/1999 | Prutchi et al. | |
| 5,995,868 A | 11/1999 | Dorfmeister | |
| 6,016,449 A | 1/2000 | Fischell et al. | |
| 6,066,163 A | 5/2000 | John | |

(Continued)

OTHER PUBLICATIONS

Adjouadi, M. et al., "Detection of Interictal Spikes and Artifactual Data Through Orthogonal Transformations," Journal of Clinical Neurophysiology, Feb. 2005, pp. 53-64, vol. 22, No. 1.

(Continued)

*Primary Examiner* — Michael R Bloch
(74) *Attorney, Agent, or Firm* — Foley & Lardner LLP

(57) ABSTRACT

Medical device systems and methods for operating medical device systems conserve energy by efficiently managing computational demands of the systems. A first analysis, having relatively lower computational processing demand than at least a second analysis, processes signals from a subject to determine a first estimate of a propensity for the subject to have a neurological event. If the first estimate meets a set of specified criteria, a second analysis is performed to determine a second estimate of the propensity for the subject to have a neurological event.

21 Claims, 8 Drawing Sheets

(56) References Cited

U.S. PATENT DOCUMENTS

| | | | |
|---|---|---|---|
| 6,161,045 A | 12/2000 | Fischell et al. | |
| 6,230,049 B1 | 5/2001 | Fischell et al. | |
| 6,304,775 B1 | 10/2001 | Iasemidis et al. | |
| 6,354,299 B1 | 3/2002 | Fischell et al. | |
| 6,360,122 B1 | 3/2002 | Fischell et al. | |
| 6,463,322 B1* | 10/2002 | Lutz | A61B 5/04004 600/544 |
| 6,560,486 B1 | 5/2003 | Osorio et al. | |
| 6,594,524 B2 | 7/2003 | Esteller et al. | |
| 6,658,287 B1* | 12/2003 | Litt | A61B 5/0476 600/544 |
| 6,990,372 B2 | 1/2006 | Perron et al. | |
| 7,089,059 B1* | 8/2006 | Pless | A61B 5/0484 607/45 |
| 7,231,254 B2 | 6/2007 | DiLorenzo | |
| 7,787,945 B2 | 8/2010 | Greene | |
| 8,002,700 B2 | 8/2011 | Ferek-Petric et al. | |
| 8,190,248 B2 | 5/2012 | Besio et al. | |
| 2002/0035338 A1 | 3/2002 | Dear et al. | |
| 2002/0103512 A1 | 8/2002 | Echauz et al. | |
| 2003/0009204 A1 | 1/2003 | Amundson et al. | |
| 2004/0054297 A1 | 3/2004 | Wingeier et al. | |
| 2005/0165323 A1* | 7/2005 | Montgomery | A61B 5/0006 600/544 |
| 2006/0293578 A1 | 12/2006 | Rennaker | |
| 2007/0150025 A1 | 6/2007 | DiLorenzo et al. | |
| 2007/0213785 A1 | 9/2007 | Osorio et al. | |
| 2007/0287931 A1* | 12/2007 | Dilorenzo | 600/545 |
| 2008/0161712 A1* | 7/2008 | Leyde | A61B 5/0006 600/544 |

OTHER PUBLICATIONS

Bergey, G.K. et al., "Epileptic Seizures are Characterized by Changing Signal Complexity," Clinical Neurophysiology, 2001, pp. 1-9, Elsevier.

Carretero-Gonzalez, R. et al., "Scaling and Interleaving of Subsystem Lyapunov Exponents for Spatio-Temporal Systems," Chaos, Jun. 1999, pp. 466-482, vol. 9, No. 2.

Casdagli, M.C. et al., "Characterizing Nonlinearity in Invasive EEG Recordings from Temporal Lobe Epilepsy," Physica D, Dec. 15, 1996, pp. 1-17, vol. 99, Issues 2-3.

Casdagli, M.C. et al., "Nonlinear Analysis of Mesial Temporal Lobe Seizures Using a Surrogate Data Technique," Epilepsia, Annual Meeting of the American Epilepsy Society, Baltimore, Maryland, Dec. 1-6, 1995, p. 142, vol. 36, Suppl. 4.

Casdagli, M.C. et al., "Non-Linearity in Invasive EEG Recordings from Patients with Temporal Lobe Epilepsy," Electroencephalography and Clinical Neurophysiology, Feb. 1997, pp. 1-10, vol. 102, Issue 2.

Chaovalitwongse, W. A. et al., "Reply to Comments on "Performance of a Seizure Warning Algorithm Based on the Dynamics of Intracranial EEG" by Winterhalder, M., Schelter, B., Achulze-Bonhage, A., Timmer, J.," Epilepsy Research, Jul. 31, 2006, pp. 82-84, vol. 72, Elsevier.

Chaovalitwongse, W. et al., "EEG Classification in Epilepsy," Jun. 30, 2004, Annals.tex, pp. 1-32, vol. 2, No. 37, Kluwer Academic Publishers, Netherlands.

Chavez, M. et al., "Spatio-Temporal Dynamics Prior to Neocortical Seizures: Amplitude Versus Phase Couplings," IEEE Transactions on Biomedical Engineering, May 2003, pp. 571-583, vol. 50 No. 5.

D'Alessandro, M. et al., "A Multi-Feature and Multi-Channel Univariate Selection Process for Seizure Prediction," Clinical Neurophysiology, 2005, pp. 506-516, vol. 116.

Drury, I. et al., "Seizure Prediction Using Scalp Electroencephalogram," Experimental Neurology, 2003, pp. S9-S18, vol. 184.

Esteller, R. et al., "A Comparison of Waveform Fractal Dimension Algorithms," IEEE Transactions on Circuits and Systems—I: Fundamental Theory and Applications, Feb. 2001, pp. 177-183, vol. 48, No. 2.

Esteller, R. et al., "Continuous Energy Variation During the Seizure Cycle: Towards an On-Line Accumulated Energy," Clinical Neurophysiology, Jan. 22, 2005, pp. 517-526, vol. 116.

Esteller, R. et al., "Feature Parameter Optimization for Seizure Detection/Prediction," IntelliMedix, Inc., [online] [Retrieved on Oct. 31, 2005] Retrieved from the Internet<URL:http://66.102.7.104/search?q=cache:4he0GuwtlacJ:icsl.m...re%2520Detection%2520Prediction.doc+intellimedix&hl=en>.

Faul, S. et al., "An Evaluation of Automated Neonatal Seizure Detection Methods," Clinical Neurophysiology, 2005, pp. 1533-1541, vol. 116.

Franaszczuk, P.J. et al., "An Autoregressive Method for the Measurement of Synchronization of Interictal and Ictal EEG Signals," Biological Cybernetics, 1999, pp. 3-9, vol. 81, Springer-Verlag.

Iasemidis, L.D. et al., "Localizing Preictal Temporal Lobe Spike Foci Using Phase Space Analysis," Abstracts of the XIIth International Congress of Electroencephalography and Clinical Neurophysiology, Rio de Janeiro, Brazil, Jan. 14-19, 1990, pp. S63-S64, vol. 75, No. 1, Elsevier Scientific Publishers Ireland, Ltd.

Iasemidis, L.D. et al., "Measurement and Quantification of Spatio-Temporal Dynamics of Human Epileptic Seizures," in Nonlinear Signal Processing in Medicine, M. Akay (Ed.), 1999, pp. 1-27, IEEE Press.

Iasemidis, L.D. et al., "Modelling of EcoG in Temporal Lobe Epilepsy," Proceedings of the 25th Rocky Mountain Bioengineering Symposium, Colorado Springs, CO, 1988, pp. 1-12.

Iasemidis, L.D. et al., "Nonlinear Dynamics of Electrocorticographic Data in Temporal Lobe Epilepsy," Journal of Clinical Neurophysiology, 1988, p. 339, vol. 5, No. 4, Raven Press.

Iasemidis, L.D. et al., "Preictal-Postictal Versus Postictal Analysis for Epileptogenic Focus Localization," J. Clin. Neurophysiol., 1997, p. 144, vol. 14.

Iasemidis, L.D. et al., "Quadratic Binary Programming and Dynamical System Approach to Determine the Predictability of Epileptic Siezures," Journal of Combinatorial Optimization, 2001, pp. 9-26, vol. 5, Kluwer Academic Publishers, Netherlands.

Iasemidis, L.D. et al., "The Use of Dynamical Analysis of EEG Frequency Content in Seizure Prediction," Society Proceedings, American EEG Society, 1993 Annual Meeting, New Orleans, LA, Oct. 11-12, 1993, Electroencephalography and Clinical Neurophysiology, 1994, p. 39P, vol. 91.

Jouny, C.C. et al., "Characterization of Epileptic Seizure Dynamics Using Gabor Atom Density," Clinical Neurophysiology, 2003, pp. 426-437, vol. 114.

Le Van Quyen, M. et al., "Preictal State Identification by Synchronization Changes in Long-Term Intracranial EEG Recordings," Clinical Neurophysiology, 2005, pp. 559-568, vol. 116.

Mormann, F. et al., "Seizure Anticipation: From Algorithms to Clinical Pratice," Current Opinion in Neurology, 2006, pp. 187-193, vol. 19, Lippincott Williams & Wilkins.

Osorio, I. et al., "Automated Seizure Abatement in Humans Using Electrical Stimulation," Ann. Neurol., 2005, pp. 258-268, vol. 57, Wiley-Liss, Inc.

Rahimi, A. et al., "On the Effectiveness of Aluminum Foil Helmets: An Empirical Study," Feb. 17, 2005, [online] [Retrieved on Dec. 13, 2005] Retrieved from the InternetURL:http://people.csail.mitedu/rahimi/helmet/.

Robinson, P.A. et al., "Steady States and Global Dynamics of Electrical Activity in the Cerebral Cortex," Phys. Rev. E, Mar. 5, 1998, 13 pages, vol. 58, Issue 3.

Schelter, B. et al., "Testing Statistical Significance of Multivariate Time Series Analysis Techniques for Epileptic Seizure Prediction," Chaos, 2006, pp. 1-10, vol. 16, No. 013108.

Schwartzkroin, P.A., "Progres in Epilepsy Research—Origins of the Epileptic State," Epilepsia, 1997, pp. 853-858, vol. 38, No. 8, Lippincott-Raven Publishers.

Shoeb, A. et al., "Patient-Specific Seizure Detection," MIT Computer Science and Artificial Intelligence Laboratory, Epilepsy & Behavior, 2004, pp. 193-194.

Terry, J.R. et al., "An Improved Algorithm for the Detection of Dynamical Interdependence in Bivariate Time-Series," Biol. Cybern., 2003, pp. 129-136, vol. 88.

(56) References Cited

OTHER PUBLICATIONS

Tsakalis, K.S., "Prediction and Control of Epileptic Seizures: Coupled Oscillator Models," Part 2, Arizona State University, no date, 28 pages.
Vonck, K. et al., "Neurostimulation for Refractory Epilepsy," Acta Neurol. Belg., 2003, pp. 213-217, vol. 103.
Wells, R.B., "Spatio-Temporal Binding and Dynamic Cortical Organization: Research Issues," Mar. 2005, pp. 1-68.
Wong, S. et al., "A Stochastic Framework for Evaluationg Seizure Prediction Algorithms Using Hidden Markov Models," J. Neurophysiol., Oct. 4, 2006, pp. 2525-2532, vol. 97.
Zhang, X. et al., "High-Resolution EEG: Cortical Potential Imaging of Interictal Spikes," Clinical Neurophysiology. 2003. DD. 1963-1973. vol. 114.
Final Office Action dated Apr. 2, 2015 in U.S. Appl. No. 11/616,793, filed Dec. 27, 2006.
Non-Final Office Action dated Jul. 17, 2014 in U.S. Appl. No. 11/616,793, filed Dec. 27, 2006.
Adjouadi, M. et al., "A New Mathematical Approach Based on Orthogonal Operators for the Detection of Interictal Spikes in Epileptogenic Data," Presented at Rocky Mountain Bioengineering Symposium & International ISA Biomedical Sciences Instrumentation Symposium, 2004, pp. 175-180.
Adjouadi, M. et al., "Interictal Spike Detection Using the Walsh Transform," IEEE Transactions on Biomedical Engineering, May 2004, pp. 868-872, vol. 51, No. 5.
Adjouadi, M. et al., "Detection of Interictal Spikes and Artifactual Data Through Orthogonal Transformations," Journal of Clinical Neurophysiolo~JY. Feb. 2005, pp. 53-64, vol. 22, No. 1.
Aksenova, T.I. et al., "On-Line Disharmony Detection for Early Prediction of Epilepsy Seizure Onset," 2003, 2 pages.
Aksenova, T.I. et al., "Nonparametric On-Line Detection of Changes in Signal Spectral Characteristics for Early Prediction of Epilepsy Seizure Onset," Journal of Automation and Information Sciences, 2004, pp. 35-45, vol. 36, No. 8.
Andrzejak, R.G. et al., "Testing the Null Hypothesis of the Nonexistence of a Preseizure State," Physical Review, 2003, pp. 1-4, The American Physical Society, vol. 67, No. 010901(R).
Andrzejak, R.G. et al., "Bivariate Surrogate Techniques: Necessity, Strengths, and Caveats," Physical Review, 2003, pp. 1-15, The American Physical Society, vol. 68, No. 066202.
Aschenbrenner-Scheibe, R. et al., "How Well Can Epileptic Seizures be Predicted? An Evaluation of a Nonlinear Method," Brain, Sep. 23, 2003, pp. 2616-2626, vol. 126.
Avanzin I, G., "Is Tolerance to Antiepileptic Drugs Clinically Relevant?" Epilepsia, 2006, pp. 1285-1287, vol. 47, No. 8, Blackwell Publishing, Inc.
Bangham, A.D. et al., "Diffusion of Univalet Ions Across the Lamellae of Swollen Phospholipids," J. Mol. Biol., 1965, pp. 238-252, vol. 13.
Baruch I, I. et al., "Functional Holography of Recorded Neuronal Networks Activity," Neuroinformatics, 2004, pp. 333-352, vol. 4.
Baruch I, I. et al., Functional Holography of Complex Networks Activity—From Cultures to the Human Brain, Complexity, 2005, pp. 38-51, vol. 10, No. 3, Wiley Periodicals, Inc.
Ben-Hur, A. et al., "Detecting Stable Clusters Using Principal Component Analysis," in Methods in Molecular Biology, 2003 pp. 1-23.
Bergey, G.K. et al., "Epileptic Seizures are Characterized by Changing Signal Complexity," Clinical Neurophysioloqy, 2001, pp. 1-9, Elsevier.
Betterton, P. et al., "Determining State of Consciousness from the Intracranial Electroencephalogram (IEEG) for Seizure Prediction," Proceedings of the 22nd IASTED International Conference Modelling, Identification and Control, Feb. 10-13, 2003, Innsbruck, Austria, pp. 313-317.
Bhattacharya, J. et al., "Enhanced Phase Synchrony in the Electroencephalography Band for Musicians While Listening to Music," Physical Review, 2001, pp. 1-4, The American Physical Society, vol. 64, No. 012902.

Boley, D. et al., "Training Support Vector Machine Using Adaptive Clustering," Proceedigns of the Fourth SIAM International Conference on Data Mining, 2004,12 pages.
Burges, C.J.C., "A Tutorial on Support Vector Machines for Pattern Recognition," Data Mining and Knowledqe Discovery, 1998, pp. 121-167, vol. 2, Kluwer Academic Publishers.
Cao, Y. et al., "Detecting Dynamical Changes in Time Series Using the Permutation Entropy," Physical Review, 2004, pp. 1-7, vol. 70, No. 046217.
Carretero-Gonzalez, R. et al., "Scaling and Interleaving of Subsystem Lyapunov Exponents for Spatia-Temporal Systems," Chaos, Jun. 1999, pp. 466-482, vol. 9, No. 2.
Casdagli, M.G. et al., "Nonlinear Analysis of Mesial Temporal Lobe Seizures Using a Surrogate Data Technique," Epilepsia, Annual Meeting of the American Epilepsy Society, Baltimore, Maryland, Dec. 1-6, 1995, p. 142, vol. 36, Suppl. 4.
Casdagli, M.G. et al., "Characterizing Nonlinearity in Invasive EEG Recordings from Temporal Lobe Epilepsy," Physica D, Dec. 15, 1996, pp. 1-17, vol. 99, Issues 2-3.
Casdagli, M.G. et al., "Non-Linearity in Invasive EEG Recordings from Patients with Temporal Lobe Epilepsy," Electroencephalography and Clinical Neurophysiology, Feb. 1997, pp. 1-10, vol. 102, Issue 2.
Cerf, R. et al., "Criticality and Synchrony of Fluctuations in Rhythmical Brain Activity: Pretransitional Effects in Epileptic Patients," Bioloqical Cybernetics, Mar. 30, 2004, pp. 239-255, vol. 903.
Chaovalitwongse, W. et al., "EEG Classification in Epilepsy," Jun. 30, 2004, Annals. lex, pp. 1-32, vol. 2, No. 37, Kluwer Academic Publishers, Netherlands.
Chaovalitwongse, W. et al., "Performance of a Seizure Warning Algorithm Based on the Dynamics of Intracranial EEG," Epilepsy Research, 2003, pp. 1-46, vol. 64, Issue 3.
Chaovalitwongse, W. A. et al., "Reply to Comments on "Performance of a Seizure Warning Algorithm Based on the Dynamics of Intracranial EEG" by Winterhalder, M., Scheller, B., Achulze-Bonhage, A., Timmer, J.," Epilepsy Research, Jul. 31, 2006, pp. 82-84, vol. 72, Elsevier.
Chávez, M. et al., "Spatia-Temporal Dynamics Prior to Neocortical Seizures: Amplitude Versus Phase Couplings," IEEE Transactions on Biomedical Engineering, May 2003, pp. 571-583, vol. 50 No. 5.
Chrichton, M., "The Terminal Man," 1972, pp. 21-24,32-33, 70-81, Alfred A. Knopf, New York.
Curry, W.J. et al., "New Antiepileptic Drugs: Gabapentin, Lamotrigine, Felbamate, Topiramate and Fosphenytoin," American Family Physician, Feb. 1, 1998, 9 pages, vol. 57, No. 3.
D'Alessandro, M. et al., "A Multi-Feature and Multi-Channel Univariate Selection Process for Seizure Prediction," Clinical Neurophysioloqy, 2005, pp. 506-516, vol. 116.
D'Alessandro, M. et al., "Epileptic Seizure Prediction Using Hybrid Feature Selection Over Multiple Intracranial EEG Electrode Contacts: A Report of Four Patients," IEEE Transactions on Biomedical Enqineerinq, May 2003, pp. 603-615, vol. 50, No. 5.
Ebersole, J.S., "In Search of Seizure Prediction: A Critique," Clinical Neurophysiology, 2005, pp. 489-492, vol. 116.
Ebersole, J.S., "Functional Neuroimaging with EEG Source Models to Localize Epileptogenic Foci Noninvasively," Neuorology, Available at http://www.uchospitals.edu/pdf/uch.sub.--001471.pdf, Accessed Feb. 28, 2006, 3 paqes.
Elbert, T. et al., "Chaos and Physiology: Deterministic Chaos in Excitable Cell Assemblies," Physiological Reviews, Jan. 1994, pp. 1-47, vol. 74, No. 1.
Elger, C. E. et al., "Nonlinear EEG Analysis and Its Potential Role in Epileptology," Epilepsia, 2000, pp. S34-S38, vol. 41, Suppl. 3.
Elger, C.E. et al., "Short Communication—Seizure Prediction by Non-Linear Time Series Analysis of Brain Electrical Activity," European Journal of Neuroscience, 1998, pp. 786-789, vol. 10.
Esteller, R. et al., "Continuous Energy Variation During the Seizure Cycle: Towards an On-Line Accumulated Enerqy," Clinical Neurophysioloqy, Jan. 22, 2005, pp. 517-526, vol. 116.
Esteller, R. et al., "Feature Parameter Optimization for Seizure Detection/Prediction," IntelliMedix, Inc., [online] [Retrieved on Oct. 31, 2005] Retrieved from the Internet<U RL: htlp://66.1 02.7

(56) References Cited

OTHER PUBLICATIONS

.1 04/search?q=cache:4heOGuwtlacJ :icsl.m...re%2520Detection%2520Prediction.doc+intellimedix&hl=en>.

Esteller, R. et al., "A Comparison of Waveform Fractal Dimension Algorithms," IEEE Transactions on Circuits and Systems—1: Fundamental Theory and Applications, Feb. 2001, pp. 177-183, vol. 48, No. 2.

Faul, S. et al., "An Evaluation of Automated Neonatal Seizure Detection Methods," Clinical Neurophysioloqy, 2005, pp. 1533-1541, vol. 116.

Fein, G. et al., "Common Reference Coherence Data are Confounded by Power and Phase Effects," Electroencephalography and Clinical Neurophysiology, 1988, pp. 581-584, vol. 69, Elsevier Scientific Publishers, Ireland, Ltd.

Fell, J. et al., "Linear Inverse Filtering Improves Spatial Separation of Nonlinear Brain Dynamics: A Simulation Study," Journal of Neuroscience Methods, 2000, pp. 49-56, vol. 98, Elsevier.

Firpi, H. et al., "Epileptic Seizure Detection by Means of Genetically Programmed Artifical Features," GECCO '05, Jun. 25-29, 2005, pp. 461-466.

Fisher, R.S. "Reassessment: Vagus Nerve Stimulation for Epilepsy," American Academy of Neurology, 1999, [online] [Retrieved on Apr. 14, 2006] Retrieved from the Internet<URL:www.neurology.org>.

Franaszczuk, P.J. et al., "An Autoregressive Method for the Measurement of Synchronization of Interictal and Ictal EEG Siqnals," Bioloqical Cybernetics, 1999, pp. 3-9, vol. 81, Sprinqer-Verlaq.

Gardner, A.B., "A Novelty Detection Approach to Seizure Analysis from Intracranial EEG," Dissertation, Georgia Institute of Technology, Apr. 2004, pp. 1-146.

Geva, A.B. et al., "Forecasting Generalized Epileptic Seizures from the EEG Signal by Wavelet Analysis and Dynamic Unsupervised Fuzzy Clustering," IEEE Transactions on Biomedical Engineering, Oct. 1998, pp. 1205-1216, vol. 45, No. 10.

Gigola, S. et al., "Prediction of Epileptic Seizures Using Accumulated Energy in a Multiresolution Framework," Journal of Neuroscience Methods, 2004, pp. 107-111, vol. 138, Elsevier.

Guyon, I. et al., "Multivariate Non-Linear Feature Selection with Kernel Multiplicative Updates and Gram-Schmidt Relief," To appear in the proceedings of the BISC FLINT-CIBI 2003 workshop, Berkeley, Dec. 2003, pp. 1-11.

Guyon, I. et al., "An Introduction to Variable and Feature Selection," Journal of Machine Learning Research, Mar. 2003, pp. 1157-1182, vol. 3.

Harrison, M.A. et al., "Accumulated Energy Revisited," Clinical Neurophysiology, 2005, pp. 527-531, vol. 116, Elsevier.

Harrison, M.A. F. et al., "Correlation Dimension and Integral do not Predict Epileptic Seizures," Chaos, 2005, pp. 1-15, vol. 15, No. 033106, American Institute of Physics.

Hearst, M.A., "Support Vector Machines," IEEE Intelligent Systems, Jul./Aug. 1998, pp. 18-28.

Hively, L.M. et al., "Detecting Dynamical Change in Nonlinear Time Series," Physics Letters A, Jul. 19, 1999, pp. 103-114, vol. 258, Elsevier.

Hively, L.M. et al., "Epileptic Seizure Forewarning by Nonlinear Techniques," Oak Ridge National Laboratory, Nov. 2000, 40 pages.

Hively, L.M. et al., "Channel-Consistent Forewarning of Epileptic Events from Scalp EEG," IEEE Transactions on Biomedical Engineering, May 2003, pp. 584-593, vol. 50, No. 5.

Hjorth, B., "Source Derivation Simplifies Topographical EEG Interpretation," Am.J. EEG Techol., 1980, pp. 121-132, vol. 20.

Hsu, C-W. et al., "A Practical Guide to Support Vector Classification," 2003, pp. 1-12.

Huynh, J.A., "Evaluation of Gene Selection Using Support Vector Machine Recursive Feature Elimination," Internship Report, May 26, 2004, pp. 1-25.

Huynh, J., "Evaluation of Gene Selection Using Support Vector Machine Recursive Feature Elimination," Powerpoint Presentation, 2004, 41 pages.

Iasemidis, L.D. et al., "Modelling of EcoG in Temporal Lobe Epilepsy," Proceedings of the 25lh Rocky Mountain Bioengineering Symposium, Colorado Springs, CO, 1988, pp. 1-12.

Iasemidis, L.D. et al., "Phase Space Topography and the Lyapunov Exponent of Electrocorticograms in Partial Seizures," Brain Topography, Mar. 1990, pp. 187-201, vol. 2, No. 3.

Iasemidis, L.D. et al., "Localizing Preictal Temporal Lobe Spike Foci Using Phase Space Analysis," Abstracts of the XIIth International Congress of Electroencephalography and Clinical Neurophysiology, Rio de Janeiro, Brazil, Jan. 14-19, 1990, pp. 863-864, vol. 75, No. 1, Elsevier Scientific Publishers Ireland, Ltd.

Iasemidis, L.D. et al., "Long-Time-Scale Temporo-Spatial Patterns of Entrainment of Preictal Electrocorticopraphic Data in Human Temporal Lobe Epilepsy," Epilepsia, Sep./Oct. 1990, p. 621, vol. 31, No. 5.

Iasemidis, L.D. et al., "The Evolution with Time of the Spatial Distribution of the Largest Lyapunov Exponent on the Human Epileptic Cortex," in Mearsuring Chaos in the Human Brain, 1991, Eds. D. Duke et al., pp. 1-27.

Iasemidis, L.D. et al., "The Use of Dynamical Analysis of EEG Frequency Content in Seizure Prediction," Society Proceedings, American EEG Society, 1993 Annual Meeting, New Orleans, LA, Oct. 11-12, 1993, Electroencephaloqraphy and Clinical Neurophysioloqy, 1994, p. 39P, vol. 91.

Iasemidis, L.D. et al., "Quantification of Hidden Time Dependencies in the EEG within the Framework of Nonlinear Dynamics," in Nonlinear Dynamical Analysis of the EEG, 1993, Eds. B.H. Jansen et al., pp. 30-47.

Iasemidis, L.D. et al., "Time Dependencies in Partial Epilpesy," Epilepsia, Abstracts from the Annual Meetinq of the American Epileptic Society, Miami, FL, Dec. 5-8, 1993, pp. 130-131, vol. 34, Suppl. 6.

Iasemidis, L.D. et al., "Time Dependencies in the Occurrences of Epileptic Seizures," Epilepsy Research, 1994, pp. 81-94, vol. 17, Elsevier.

Iasemidis, L.D. et al., "Spatiotemporal Evolution of Dynamical Measures Precedes Onset of Mesial Temporal Lobe Seizures," Epilepsia, Abstracts from the Annual Meeting of the American Epilepsy Society, New Orleans, LA, Dec. 2-8, 1994, p. 133, vol. 35, Suppl. 8.

Iasemidis, L.D. et al., "Spatiotemporal Dynamics of Human Epileptic Seizures," in Proceedings of the 3rd Experimental Chaos Conference, 1996, R.G. Harrison et al. (Eds. ), pp. 26-30.

Iasemidis, L.D. et al., "Chaos Theory and Epilepsy," 1996, pp. 1-13.

Iasemidis, L.D. et al., "Detection of the Preictal Transition State in Scalp-Sphenoidal EEG Recordings," Journal of Clinical Neurophysiology, Sep. 1996, pp. 443-444, vol. 13, No. 5.

Iasemidis, L.D. et al., "Preictal Entrainment of a Critical Cortical Mass is a Necessary Condition for Seizure Occurrence," Epilepsia, Abstracts from the Annual Meeting of the American Epilepsy Society, San Francisco, CA, Dec. 7-10, 1996, p. 90, vol. 37, Suppl. 5.

Iasemidis, L.D. et al., "Spatiotemporal Transition to Epileptic Seizures: A Nonlinear Dynamical Analysis of Scalp and Intracranial EEG Recordings," Spatiotemporal Models in Biological and Artificial Systems, F.L. Silva et al. (Eds.), 1997, pp. 81-88, IOS Press.

Iasemidis, L.D. et al., "Epileptogenic Focus Localization by Dynamic Analysis of Interictal Periods of EEG in Patients with Temporal Lobe Epilepsy," Epilepsia, Abstracts from the Annual Meeting of the American Epilepsy Society, Boston, MA, Dec. 7-10, 1997, p. 213, vol. 38, Suppl. 8.

Iasemidis, L.D. et al., "Preictai-Postictal Versus Postictal Analysis for Epileptogenic Focus Localization," J. Clin. Neurophysiol., 1997, p. 144, vol. 14.

Iasemidis, L.D. et al., "Dynamical Interaction of the Epileptogenic Focus with Extrafocal Sites in Temporal Lobe Epilepsy," Annals of Neurology, Sep. 1997, p. 429, vol. 42, No. 3.

Iasemidis, L.D. et al., "Automated Seizure Prediction Paradigm," Epilepsia, Abstracts from the Annual Meeting of the American Epilepsy Society, San Diego, CA, Dec. 6-9, 1998, p. 207, vol. 39, Suppl. 6.

(56) References Cited

OTHER PUBLICATIONS

Iasemidis, L.D. et al., "Measurement and Quantification of Spatia-Temporal Dynamics of Human Epileptic Seizures," in Nonlinear Signal Processing in Medicine, M. Akay (Ed.), 1999, pp. 1-27, IEEE Press.
Iasemidis, L.D. et al., "Quadratic Binary Programming and Dynamical System Approach to Determine the Predictability of Epileptic Seizures," Journal of Combinatorial Optimization, 2001, pp. 9-26, vol. 5, Kluwer Academic Publishers, Netherlands.
Iasemidis, L.D., "Epileptic Seizure Prediction and Control," IEEE Transactions on Biomedical Engineering, May 2003, pp. 549-558, vol. 50, No. 5.
Iasemidis, L.D. et al., "Adaptive Epileptic Seizure Prediction System," IEEE Transactions on Biomedical Engineering, May 2003, pp. 616-627, vol. 50, No. 5.
Iasemidis, L.D. et al., "Comment on Inability of Lyapunov Exponents to Predict Epileptic Seizures," Physical Review Letters, Jan. 14, 2005, 1 paqe, PRL 94, 019801.
Iasemidis, L.D. et al., "Long-Term Prospective On-Line Real-Time Seizure Prediction," Clinical Neurphysiology, 2005, pp. 532-544, vol. 116.
Jerger, K.K. et al., "Early Seizure Detection," Journal of Clinical Neurphysiology, 2001, pp. 259-268, vol. 18, No. 3.
Jerger, K.K. et al., "Multivariate Linear Discrimination of Seizures," Clinical Neurophysiology, 2005, pp. 545-551, vol. 116.
Jouny, C. C. et al., "Characterization of Epileptic Seizure Dynamics Using Gabor Atom Density," Clinical Neurophysioloqy, 2003, pp. 426-437, vol. 114.
Jouny, C.C. et al., "Signal Complexity and Synchrony of Epileptic Seizures: Is There an Identifiable Preictal Period?" Clinical Neurophysiology, 2005, pp. 552-558, vol. 116.
Kapiris, P.G. et al., "Similarities in Precursory Features in Seismic Shocks and Epileptic Seizures," Europhysics Letters, Feb. 15, 2005, pp. 657-663, vol. 69, No. 4.
Katz, A. et al., "Does Interictal Spiking Change Prior to Seizures?" Electroencephalography and Clinical Neurophysiology, 1991, pp. 153-156, vol. 79, Elsevier Scientific Publishers Ireland Ltd.
Kerem, D.H. et al., "Forecasting Epilepsy from the Heart Rate Signal," Medical & Biological Engineering & Computing, 2005, pp. 230-239, vol. 43.
Khalilov, I. et al. "Epilptogenic Actions of GABA and Fast Oscillations in the Developing Hippocampus," Neuron, Dec. 8, 2005, pp. 787-796, vol. 48, Elsevier Inc.
Korn, H. et al., "Is there Chaos in the Brain? II. Experimental Evidence and Related Models," C.R. Biologies, 2003, pp. 787-840, vol. 326.
Kraskov, A., "Synchronization and Interdependence Measures and their Applications to the Electroencephalogram of Epilepsy Patients and Clustering of Data," Dissertation (PhD Thesis), Publication Series of the John von Neumann Institute for Computing (NIC), NIC Series, Feb. 2004, 106 pages, vol. 24.
Kreuz, T. et al., "Measure Profile Surrogates: A Method to Validate the Performance of Epileptic Seizure Prediction Algorithms," Jun. 15, 2004, Physical Review, pp. 1-9, vol. 69, No. 061915.
Lachaux, J-P. et al., "Measuring Phase Synchrony in Brain Signals," Human Brain Mapping, 1999, pp. 194-208, vol. 8.
Lai, Y-C. et al., "Inability of Lyapunov Exponents to Predict Epileptic Seizures," Physical Review Letters, Aug. 8, 2003, pp. 1-4, vol. 91, No. 6.
Lai, Y-C. et al., "Controlled Test for Predictive Power of Lyapunov Exponents: Their Inability to Predict Epileptic Seizures," Chaos, Sep. 2004, pp. 630-642, vol. 14, No. 3.
Laroche, S.M. et al., "The New Antiepileptic Drugs," Scientific Review, JAMA, Feb. 4, 2004, pp. 605-614, vol. 291, No. 5.
Latka, M. et al., "Wavelet Analysis of Epileptic Spikes," Dec. 22, 2002, pp. 1-6.
Levan Quyen, M., "Anticipating Epileptic Seizures: From Mathematics to Clinical Applications," C.R. Biologies, 2004, pp. 1-12.

Levan Quyen, M. et al., "Pre ictal State Identification by Synchronization Changes in Long-Term Intracranial EEG Recordings," Clinical Neurophysioloqy, 2005, pp. 559-568, vol. 116.
Levan Quyen, M. et al., "Nonlinear Analyses of Interictal EEG Map the Brain Interdependences in Human Focal Epilepsy," Physica D, 1999, pp. 250-266, vol. 127, Elsevier.
Levan Quyen, M. et al., "Anticipating Epileptic Seizures in Real Time by a Non-Linear Analysis of Similarity Between EEG Recordinqs," NeuroReport, Jul. 13, 1999, pp. 2149-2155, vol. 10, No. 10.
Levan Quyen, M. et al., "Comparison of Hilbert Transform and Wavelet Methods for the Analysis of Neuronal Synchrony," Journal of Neuroscience Methods, 2001, pp. 83-98, vol. 111, Elsevier.
Levan Quyen, M. et al., "Authors' Second Reply," Correspondence, The Lancet, Mar. 15, 2003, p. 971, vol. 361.
Lehnertz, K. et al., "The First International Collaborative Workshop on Seizure Prediction: Summary and Data Description," Clinical Neurophysiology, 2005, pp. 493-505, vol. 116, Elsevier.
Lehnertz, K., "Non-Linear Time Series Analysis of Intracranial EEG Recordings in Patients with Epilepsy—An Overview," International Journal of Psychophysiology, 1999, pp. 45-52, vol. 34, Elsevier.
Lehnertz, K. et al., "Nonlinear EEG Analysis in Epilepsy: Its Possible Use for Interictal Focus Localization, Seizure Anticipation, and Prevention," Journal of Clinical Neurophysiology, 2001, pp. 209-222, vol. 18, No. 3.
Lehnertz, K. et al., "Seizure Prediction by Nonlinear EEG Analysis," IEEE Engineering in Medicine and Biology Magazine, Jan./Feb. 2003, pp. 57-63.
Lemos, M.S. et al., "The Weighted Average Reference Montage," Electroencephalography and Clinical Neurophysiology, 1991, pp. 361-370, vol. 79, Elsevier Scientific Publishers Ireland, Ltd.
Li, D. et al., "Non-Linear, Non-Invasive Method for Seizure Anticipation in Focal Epilepsy," Mathematical Biosciences, 2003, pp. 63-77, vol. 186, Elsevier.
Li, D. et al, "Linear and Nonlinear Measures and Seizure Anticipation in Temporal Lobe Epilepsy," Journal of Computational Neuroscience, 2003, pp. 335-345, vol. 15, Kluwer Academic Publishers, Netherlands.
Li, X. et al, "Fractal Spectral Analysis of Pre-Epileptic Seizures in Terms of Criticality," Journal of Neural Engineering, Mar. 8, 2005, pp. 11-16, vol. 2.
Litt, B. et al., "Prediction of Epileptic Seizures," Neurology, The Lancet, May 2002, pp. 22-30, vol. 1, No. 1.
Litt, B. et al., "Seizure Prediction and the Preseizure Period," Current Opinion in Neurology, 2002 pp. 173-177, vol. 15.
Maiwald, T. et al., "Comparison of Three Nonlinear Seizure Prediction Methods by Means of the Seizure Prediction Characteristic," Physica D, 2004, pp. 357-368, vol. 194.
Mangasarian, O.L. et al., "Lagrangian Support Vector Machines," Mar. 9, 2006, pp. 1-22.
Martinerie, J. et al., "Epileptic Seizures can be Anticipated by Non-Linear Analysis," Nature Medicine, Oct. 1998, pp. 1173-1176, vol. 4, No. 10.
Mcsharry, P.E., "Detection of Dynamical Transitions in Biomedical Signals Using Nonlinear Methods," in Knowledge-Based Intelligent Information and Engineering Systems, 2004, pp. 483-490.
Mcsharry, P.E. et al., "Linear and Non-Linear Methods for Automatic Seizure Detection in Scalp Electro-Encephalogram Recordings," Medical & Biological Engineering & Computing. 2002, pp. 447-461, vol. 40.
Mcsharry, P.E. et al., "Comparison of Predictability of Epileptic Seizures by a Linear and a Nonlinear Method," IEEE Transactions on Biomedical Engineering, May 2003, pp. 628-633, vol. 50, No. 5.
Meng, L. et al., "Gaussian Mixture Models of EcoG Signal Features for Improved Detection of Epileptic Seizures," Medical Engineering & Physics, 2004, pp. 379-393, vol. 26, Elsevier.
Mizuno-Matsumoto, Y. et al., "Wavelet-Crosscorrelation Analysis Can Help Predict Whether Bursts of Pulse Stimulation Will Terminate Afterdischarges," Clinical Neurophysiology, 2002, pp. 33-42, No. 113, Elsevier.
Mormann, F. et al., "Automated Detection of a Preseizure State Based on a Decrease in Synchronization in Intracranial Electroen-

(56) References Cited

OTHER PUBLICATIONS cephalogram Recordings from Epilepsy Patients," Physical Review, Feb. 26, 2003, vol. 67, No. 021912, The American Physical Society.

Mormann, F. et al., "Epileptic Seizures are Preceded by a Decrease in Synchronization," Epilepsy Research, 2003, pp. 173-185, vol. 53.

Mormann, F. et al., "On the Predictability of Epileptic Seizures," Clinical Neurophysiology, 2005, pp. 569-587, vol. 116, Elsevier.

Mormann, F. et al., "Seizure Anticipation: From Algorithms to Clinical Practice," Current Opinion in Neurology, 2006, pp. 187-193, vol. 19, Lippincott Williams & Wilkins.

Mormann, F. et al., "Seizure Prediction: The Long and Winding Road," Brain, 2007, pp. 314-333, vol. 130.

Mormann, F. et al., "Mean Phase Coherence as a Measure for Phase Synchronization and its Application to the EEG of Epilepsy Patients," Physica D, 2000, pp. 358-369, vol. 144, Elsevier.

Navarro, V. et al., "Seizure Anticipation in Human Neocortical Partial Epilepsy," Brain, 2002, pp. 640-655, vol. 125.

Navarro, V. et al., "Seizure Anticipation: Do Mathematical Measures Correlate with Video-EEG Evaluation?" Epilepsia, 2005, pp. 385-396, vol. 46, No. 3.

Niederhauser, J.J. et al., "Detection of Seizure Precursors from Depth-EEG Using a Sign Periodogram Transform," IEEE Transactions on Biomedical Engineering, Apr. 2003, pp. 449-458, vol. 51, No. 4.

Nigam, V. et al., "A Neural-Network-Based Detection of Epilepsy," Neurological Research, Jan. 2004, pp. 55-60, vol. 26.

Ochoa, J.G. et al., "Antiepileptic Drugs: An Overview," eMedicine.com, WebMD, updated Sep. 26, 2006, 26 pages.

Osorio, I. et al., "Real-Time Automated Detection and Quantitative Analysis of Seizures and Short-Term Prediction of Clinical Onset," Epilepsia, 1998, pp. 615-627, vol. 39, No. 6.

Osorio, I. et al., "Performance Reassessment of a Real-Time Seizure-Detection Algorithm on Long ECoG Series," Epilepsia, 2002, pp. 1522-1535, vol. 43, No. 12.

Osorio, I. et al., "Automated Seizure Abatement in Humans Using Electrical Stimulation," Ann. Neural., 2005, pp. 258-268, vol. 57, Wiley-Liss, Inc.

Ossadtchi, A. et al., "Hidden Markov Modelling of Spike Propagation from Interictal MEG Data," Physics in Medicine and Biology, Jul. 6, 2005, pp. 3447-3469, vol. 50, Institute of Physis Publishing.

Pflieger, M.E. et al., "A Noninvasive Method for Analysis of Epileptogenic Brain Connectivity," Presented at the American Epilepsy Society 2004 Annual Meeting, New Orleans, LA, Dec. 6, 2004, pp. 1-12.

Pittman, V., "Flexible Drug Dosing Produces Less Side-Effects in People with Epilepsy," Medical News Today Article, Dec. 29, 2005, [online] [Retrieved on Apr. 17, 2006] Retrieved from the Internet<URL: http://www.medicalnewstoday.com/printerfriend lynews.php?newsid=35478>.

Platt, J.C., "Using Analytic QP and Sparseness to Speed Training of Support Vector Machines," To Appear in Advances in Neural Information Processing Systems, M.S. Kearns et al. (Eds. ), 1999, pp. 1-8, MIT Press.

Platt, J.C. et al., "Large Margin DAGs for Multiclass Classification," MIT Press, 2000, S.A. Solla et al. (Eds.), pp. 547-553.

Protopopescu, V.A. et al., "Epileptic Event Forewarning from Scalp EEG," Journal of Clinical Neurphysioloqy, 2001, pp. 223-245, vol. 18, No. 3., Lippincott Williams & Wilkins, Inc.

Remington's, 18th Edition, A.R. Gennaro (Ed.), Pharmaceutical Sciences, 1990, 5 pages, Mack Publishing Company.

Robinson, P.A. et al., "Steady States and Global Dynamics of Electrical Activity in the Cerebral Cortex," Phvs. Rev. E, Mar. 5, 1998, 13 pages, vol. 58, Issue 3.

Rudrauf, D. et al., "Frequencey Flows and the Time-Frequency Dynamics of Multivariate Phase Synchronization in Brain Signals," NeuroImage, 2005, pp. 1-19.

Saab, M.E. et al., "A System to Detect the Onset of Epileptic Seizures in Scalp EEG," Clinical Neurophysioloqy, 2005, pp. 427-442, vol. 116, Elsevier.

Sackellares, J.C. et al., "Epilepsy—When Chaos Fails," in Chaos in the Brain? K. Lehnertz et al. (Eds.), Jan. 3, 2000, pp. 1-22.

Sackellares, J.C. et al., "Measurement of Chaos to Localize Seizure Onset," Epilepsia, Sep./Oct. 1989, p. 663, vol. 30, No. 5.

Sackellares, J.C. et al., "Computer-Assisted Seizure Detection Based on Quantitative Dynamical Measures," Electroencephalography and Clinical Neurophysiology, 1995, p. 18P, vol. 95, No. 2.

Sackellares, J.C. et al., "Dynamical Studies of Human Hippocampus in Limbic Epilepsy," Neurology, Apr. 1995, p. A404-A405, vol. 45, Suppl. 4.

Sackellares, J.C. et al., "Relationship Between Hippocampal Atrophy and Dynamical Measures of EEG in Depth Electrode Recordings," Electroencephalography and Clinical Neurophysiology, Jan. 1997, vol. 102, No. 1.

Sackellares, J.C. et al., "Epileptic Seizures as Neural Resting Mechanisms," Epilepsia, Abstracts from the 22nd International Epilepsy Congress, Dublin Ireland, Jun. 29-Jul. 4, 1997, 1 page, vol. 38, Suppl. 3, Lippincott-Raven Publishers.

Sackellares, J.C. et al., "Predictability Analysis for an Automated Seizure Prediction Algorithm," Journal of Clinical Neurophysiology, Dec. 2006, pp. 509-520, vol. 23, No. 6.

Salant, Y. "Prediction of Epileptic Seizures from Two-Channel EEG," Medical & Biological Engineering & Computing, Sep. 1998, pp. 549-556, vol. 36.

Schelter, B. et al., "Testing for Directed Influences Among Neural Signals Using Partial Directed Coherence," Journal of Neuroscience Methods, 2005, pp. 1-10, Elsevier.

Schindler, K. et al., "EEG Analysis with Simulated Neuronal Cell Models Helps to Detect Pre-Seizure Changes," Clinical Neurophysiology, 2002, pp. 604-614, vol. 113, Elsevier.

Schwartzkroin, P.A., "Progress in Epilepsy Research—Origins of the Epileptic State," Epilepsia, 1997, pp. 853-858, vol. 38, No. 8, Lippincott-Raven Publishers.

Sheridan, T.B., "Humans and Automation—System Design and Research Issues," HFES Issues in Human Factors and Ergomonics Series, 2002, 6 pages, vol. 3, John Wiley & Sons, Inc.

Shoes, A. et al., "Patient-Specific Seizure Detection," MIT Computer Science and Artificial Intelligence Laboratory, Epilepsy & Behavior, 2004, pp. 193-194.

Staba, R.J. et al., "Quantitative Analysis of High-Frequency Oscillations (80-500Hz) Recorded in Human Epileptic Hippocampus and Entorhinal Cortex," J. Neurophysiology, 2002, pp. 1743-1752, vol. 88.

Stefanski, A. et al., "Using Chaos Synchronization to Estimate the Largest Lyapunov Exponent of Nonsmooth Systems," Discrete Dynamics in Nature and Society, 2000, pp. 207-215, vol. 4.

Subasi, A. et al., "Classification of EEG Signals Using Neural Network and Logistic Regression," Computer Methods and Programs in Biomedicine, 2005, pp. 87-99, vol. 78, Elsevier.

Szoka, Jr., F. et al., "Procedure for Preparation of Liposomes with Large Internal Aqueous Space and High Capture by Reverse-Phase Evaporation," Proc. Natl. Acad. Sci., Sep. 1978, pp. 4194-4198, vol. 75, No. 9.

Tass, P. et al., "Detection of n:m Phase Locking from Noisy Data: Application to Magnetoencephalography," Physical Review Letters, Oct. 12, 1998, pp. 3291-3294, vol. 81, No. 15.

Terry, J.R. et al., "An Improved Algorithm for the Detection of Dynamical Interdependence in Bivariate Time-Series," Bioi. Cybern., 2003, pp. 129-136, vol. 88.

Tetzlaff, R. et al., "Cellular Neural Networks (CNN) with Linear Weight Functions for a Prediction of Epileptic Seizures," International Jounal of Neural Systems, 2003, pp. 489-498, vol. 13, No. 6, World Scientific Publishing Company.

Theiler, J. et al., "Testing for Nonlinearity in Time Series: the Method of Surrogate Data," Physica D, 1992, pp. 77-94, vol. 58.

Tsakalis, K.S., "Prediction and Control of Epileptic Seizures: Coupled Oscillator Models," Arizona State University, no date, 53 paqes.

Tsakalis, K.S., "Prediction and Control of Epileptic Seizures: Coupled Oscillator Models," Part 1, Arizona State University, no date, 25 pages.

Van Drongelen, W. et al., "Seizure Anticipation in Pediatric Epilepsy: Use of Kolmogorov Entropy," Pediatric Neurology, 2003, pp. 207-213, vol. 29, No. 3.

(56) References Cited

OTHER PUBLICATIONS

Vanputten, M.J.A.M., "Nearest Neighbor Phase Synchronization as a Measure to Detect Seizure Activity from Scalp EEG Recordinqs," Journal of Clinical Neurophysiology, 2003, pp. 320-325, vol. 20, No. 5.

Venugopal, R. et al., "A New Approach Towards Predictability of Epileptic Seizures: KL T Dimension," ISA, 2003, Paper #2003-022, pp. 123-128.

Vonck, K. et al., "Long-Term Amygdalohippocampal Stimulation for Refractory Temporal Lobe Epilepsy," Annals of Neurolology, Nov. 2002, pp. 556-565, vol. 52, No. 5.

Vonck, K. et al., "Neurostimulation for Refractory Epilepsy," Acta Neural. Belg., 2003, pp. 213-217, vol. 103.

Vonck, K. et al., "Long-Term Deep Brain Stimulation for Refractory Temporal Lobe Epilepsy," Epilepsia, 2005, pp. 98-99, vol. 46, Suppl. 5.

Weiss, P., "Seizure Prelude Found by Chaos Calculation," ScienceNewsOnline, May 23, 1998, [online] [Retrieved on Oct. 18, 2005] Retrieved from the Internet<URL:http://www.sciencenews.orq/paqes/sn arc98/5 23 98/fob2.htm>.

Wells, R.B., "Spatia-Temporal Binding and Dynamic Cortical Organization: Research Issues," Mar. 2005, pp. 1-68.

Widman, G. et al., "Reduced Signal Complexity of Intracellular Recordings: A Precursor for Epileptiform Activity?" Brain Research, 1999, pp. 156-163, vol. 836, Elsevier.

Winterhalder, M. et al., "The Seizure Prediction Characteristic: A General Framework to Assess and Compare Seizure Prediction Methods," Epilepsy & Behavior, 2003, pp. 318-325, vol. 4.

Winterhalder, M. et al., "Sensitivity and Specificity of Coherence and Phase Synchronization Analysis," Dec. 28, 2004, pp. 1-21.

Wong, S. et al., "A Stochastic Framework for Evaluating Seizure Prediction Algorithms Using Hidden Markov Models," J. Neurophysiol., Oct. 4, 2006, pp. 2525-2532, vol. 97.

Yang, H-J. et al., "Relation Between Responsiveness to Neurotransmitters and Complexity of Epileptiform Activity in Rat Hippocampal CA1 Neurons," Epilepsia, 2002, pp. 1330-1336, vol. 43, No. 11.

Yang, K. et al., "CleVer: A Feature Subset Selection Technique for Multivariate Time Series," PAKDD 2005, LNAI 3518, T.B. Ho et al. (Eds.), 2005, pp. 516-522, Springer-Verlag.

Yang, K. et al., "A Supervised Feature Subset Selection Technique for Multivariate Time Series," Proceedings of the Workshop on Feature Selection for Data Mining, 2005 SIAM International Conference on Data Mining, Apr. 23, 2005, Newport Beach, CA, 10 pages.

Yang, M.C.K. et al., "Testing Whether a Prediction Scheme is Better Than Guess," Chapter 14, Quantitative Neuroscience, 2004, pp. 251-262, Springer.

Yatsenko, V. et al., "Geometric Models, Fiber Bundles and Biomedical Applications," Proceedings of Institure of Mathematics of NAS of Ukraine, 2004, pp. 1518-1525, vol. 50, Part 3.

Zhaveri, H.P. et al., "Time-Frequency Analyses of Non-Stationary Brain Signals," Electroencephalography & Clinical Neurophysioloqy, Aug. 1991, pp. 28P-29P, vol. 79, No. 2.

Zhang, X. et al., "High-Resolution EEG: Cortical Potential Imaging of Interictal Spikes," Clinical Neurophysiology, 2003, pp. 1963-1973, vol. 114.

\* cited by examiner

LOW POWER DEVICE WITH CONTINGENT SCHEDULING

CROSS-REFERENCE TO RELATED APPLICATIONS

This application is a divisional of U.S. patent application Ser. No. 11/616,788 filed Dec. 27, 2006, the disclosure of which is incorporated herein by reference in its entirety.

FIELD

The present invention relates generally to medical device systems.

BACKGROUND

A variety of medical device systems are used to measure physiological signals from a subject and to process the signals and provide indications of potential or actual problem conditions. Computational demands of processing systems associated with the medical devices systems produce drains on the power sources of these device systems and can have a major impact on overall battery life. Moreover, in many medical device systems, it is desirable to keep the system as small and unobtrusive as possible so that the patient can have it available at all times.

In the case of implantable systems, power source replacement may involve surgery with its attendant costs and risks to the subject. Moreover, power source replacement may involve replacement of the implantable system itself because such units are typically hermetically sealed to reduce the likelihood of infection.

SUMMARY

The invention provides medical device systems and methods for operating medical device systems that provide energy savings by efficiently managing computational demands of the systems. Some such systems comprise detectors to receive input from a subject, communications systems to deliver signals indicative of the input to a processor, processing systems to analyze the signals and determine one or more conditions of the subject, and a communication system to provide indications of the one or more conditions to the subject.

The various embodiments describe ways for a medical device to provide at least two stages of processing for signals measured from a subject. A first set of computer instructions, programmable logic, or circuitry, for example, one or more feature extractors and one or more classifiers process the signals to determine a first estimate of a susceptibility or propensity of the subject to have a neurological event. If the first estimate meets a set of criteria, a second set of computer instructions, programmable logic or circuitry, typically more computationally demanding and/or more sensitive and possibly providing more specific results than the first, is enabled to determine a second estimate of the propensity for the subject to have a neurological event. At least one of the feature extractors may be selected based on information about the subject. If desired, information related to the estimate may be output to the subject. The systems and method can proceed in such a manner for any number of iterations. For example, a third set of computer instructions, programmable logic or circuitry may be enabled if the second estimate meets a second set of criteria, and so forth. Information related to the estimate may be output to the subject. The computer instructions, programmable logic or circuitry may be enabled on a processing system that is external to the subject, on a processing system that is implanted in the subject, or on combinations of external and implanted processing systems.

DETAILED DESCRIPTION

Figure 1:
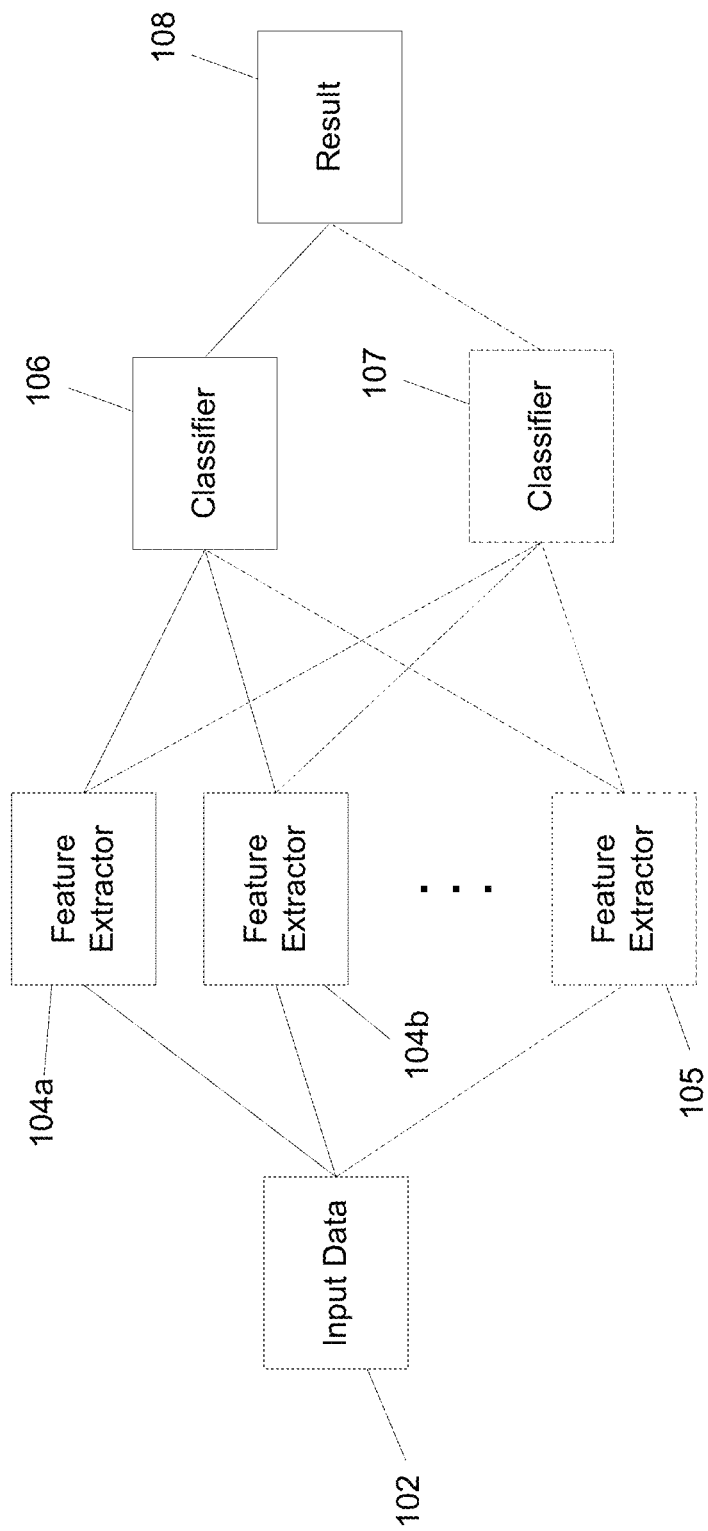
FIG. 1 is a block diagram illustrating aspects of contingent use of feature extractors and classifiers.

Certain specific details are set forth in the following description and figures to provide an understanding of various embodiments of the invention. Certain well-known details, associated electronics and medical devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

As described in the background, a variety of medical device systems are used to measure physiological signals from a subject and to process those signals. Some such medical device systems, especially those comprising ambulatory and implantable devices, operate on portable power sources such as batteries. Computational processing demands, especially in the case of substantially continuous or repeated monitoring of the subject, can cause energy drains and may have a negative impact on battery life. The various embodiments of the systems and methods provided herein reduce the computational burden on such systems to extend the battery life.

Although some of the discussion below focuses on measuring electroencephalogram ("EEG") signals of subjects and subject populations for the detection and prediction of epileptic seizures, it should be appreciated that the invention is not limited to measuring EEG signals or to predicting epileptic seizures. For example, the invention could also be used in systems that measure one or more of a blood pressure, pulse oximetry, temperature of the brain or of portions of the subject, blood flow measurements, ECG/ electrocardiogram ("EKG"), heart rate signals, respiratory signals, chemical concentrations of neurotransmitters, chemical concentrations of medications, pH in the blood, or other physiological or biochemical parameters of a subject.

Furthermore, aspects of the invention may be useful for monitoring and assisting in the treatments for a variety of conditions such as sleep apnea and other sleep disorders, migraine headaches, depression, Alzheimer's, Parkinson's Disease, dementia, attention deficit disorder, stroke, eating disorders, other neurological or psychiatric disorders, cardiac disease, diabetes, cancer, or the like.

Using epilepsy as an illustrative example, epilepsy is a disorder of the brain characterized by neurological events in the form of chronic, recurring seizures and affects an estimated 50 million people worldwide. Seizures are a result of uncontrolled discharges of electrical activity in the brain. A seizure typically manifests itself as sudden involuntary, disruptive, and often destructive sensory, motor, and cognitive phenomena. Epilepsy is usually treated, though not cured, with medication. Surgery may be indicated in cases in which seizure focus is identifiable, and the seizure focus is not located in the eloquent cortex.

A single neurological event most often does not cause significant morbidity or mortality, but severe or recurring neurological events can result in major medical, social, and economic consequences. Epilepsy is more often diagnosed in children and young adults. People with uncontrolled epilepsy are often significantly limited in their ability to work in many industries and may not be able to legally drive an automobile.

The cause of epilepsy is often uncertain. Symptomatic epilepsies arise due to some structural or metabolic abnormality of the brain and may result from a wide variety of causes including genetic conditions, stroke, head trauma, complications during pregnancy or birth, infections such as bacterial or viral encephalitis, or parasites. Idiopathic epilepsies are those for which no other condition has been implicated as a cause and are often genetic and generalized. In the majority of cases, the cause of a subject's epilepsy is unknown.

One of the most disabling aspects of neurological disorders such as epilepsy is the seeming unpredictability of neurological events such as seizures. Mechanisms underlying the generation of seizures are thought to operate over a period of seconds to minutes before the clinical onset of a seizure. Typically, electrographic manifestations of a neurological event are detectible some time before clinical manifestations occur. Most work in the quantitative analysis of neurological events has been aimed at detecting these electrographic manifestations. NeuroPace, Inc. has been developing systems to detect the electrographic onset of a neurological event so that some action, such as direct electrical stimulation of certain brain structures, may be taken in an attempt to preempt the clinical onset of a neurological event. However, the detection of the electrographic onset of a neurological event may not come far enough in advance of the clinical onset for electrical stimulation or other therapies, such as the administration of anticonvulsant drugs, to be effective in preventing the clinical onset. Additionally, seizure activity may already be causing harm to the brain before the clinical onset of the seizure.

It is desirable to be able to predict neurological events well before their electrographic onset. Embodiments of predictive systems generally comprise a collection of detectors for acquiring data from a subject and an analysis system for processing the data. Predictive analysis systems are routinely considered to be comprised of arrangements of feature extractors and classifiers. Feature extractors are used to quantify or characterize certain aspects of the measured input signals. Classifiers are then used to combine the results obtained from the feature extractors into an overall answer or result. Systems may be designed to detect different types of conditions that may be reflective of neural condition. These could include, but are not limited to, systems designed to detect if the subject's neural condition is indicative of an increased susceptibility or propensity for a neurological event or systems designed to detect deviation from a normal condition. As can be appreciated, for other neurological or non-neurological disorders, the classification of the subject's neural condition will be based on systems, feature extractors and classifiers that are deemed to be relevant to the particular disorder.

FIG. 1 depicts an example of the overall structure of a system for estimating a propensity for the onset of a neurological event such as, for example, an epileptic seizure. The input data 102 may comprise representations of physiological signals obtained from monitoring a subject. Any number of signal channels may be used. Examples of physiological signals that may be used as input data 102 include, but are not limited to, electrical signals generated by electrodes placed on or within the brain or nervous system (EEG signals), temperature of the brain or of portions of the brain, blood pressure or blood flow measurements, pulse oximetry, ECG/EKG, blood pH, chemical concentrations of neurotransmitters, chemical concentrations of medications, combinations of the preceding, and the like.

The input data may be in the form of analog signal data or digital signal data that has been converted by way of an analog to digital converter (not shown). The signals may also be amplified, preprocessed, and/or conditioned to filter out spurious signals or noise. For purposes of simplicity the input data of all of the preceding forms is referred to herein as input data 102.

The input data 102 from the selected physiological signals is supplied to one or more feature extractors 104a, 104b, 105. A feature extractor 104a, 104b, 105 may be, for example, a set of computer executable instructions stored on a computer readable medium, or a corresponding instantiated object or process that executes on a computing device. Certain feature extractors may also be implemented as programmable logic or as circuitry. In general, a feature extractor 104a, 104b, 105 can process data 102 and identify some characteristic of the data 102. Such a characteristic of the data is referred to herein as an extracted feature.

Operation of a feature extractor 104a, 104b, 105 requires expenditure of electrical energy to process data and identify characteristics. The amount of electrical energy required may depend on the complexity, quantity, and quality of the input data and on the complexity of the processing system applied to the input data. Feature extractors 104a, 104b, 105 that are more complex generally require correspondingly larger amounts of electrical energy. As described more fully below, in some embodiments, some feature extractors 105 may be optionally applied or omitted in various circumstances. For example, when the application of one set of feature extractors 104a, 104b is sufficient to estimate that a propensity for a neurological event is sufficiently low, then other feature extractors 105 may not be applied to the input data 102. If the set of feature extractors 104a, 104b indicates a higher propensity for a neurological event, then additional feature extractors 105 may be applied to the input data 102.

Each feature extractor 104a, 104b, 105 may be univariate (operating on a single input data channel), bivariate (operating on two data channels), or multivariate (operating on multiple data channels). Some examples of potentially useful characteristics to extract from signals for use in determining the subject's propensity for a neurological event, include but are not limited to, alpha band power (8-13 Hz), beta band power (13-18 Hz), delta band power (0.1-4 Hz), theta band power (4-8 Hz), low beta band power (12-15 Hz), mid-beta band power (15-18 Hz), high beta band power (18-30 Hz), gamma band power (30-48 Hz), second, third and fourth (and higher) statistical moments of the EEG amplitudes, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STLmax, T-index, angular frequency, and entropy), line length calculations, area under the curve, first, second and higher derivatives, integrals, or a combination thereof. Of course, for other neurological conditions, additional or alternative characteristic extractors may be used with the systems described herein.

The extracted characteristics can be supplied to one or more classifiers 106, 107. Like the feature extractors 104a, 104b, 105, each classifier 106, 107 may be, for example, a set of computer executable instructions stored on a computer readable medium or a corresponding instantiated object or process that executes on a computing device. Certain classifiers may also be implemented as programmable logic or as circuitry. Operation of a classifier 106, 107 requires electrical energy. The classifiers can vary in complexity. Classifiers 106, 107 that are more complex may require correspondingly larger amounts of electrical energy. In some embodiments, some classifiers may be optionally applied or omitted in various circumstances. For example, when the application of one or more classifiers 106 is sufficient to estimate that a propensity for a neurological event is sufficiently low, then other classifiers 107 may not be applied to the extracted characteristics. If the classifiers 106 indicate a higher propensity for a neurological event, then additional classifiers 107 may be applied to the extracted characteristics.

The classifiers 106, 107 analyze one or more of the extracted characteristics and possibly other subject dependent parameters to provide a result 108 that may characterize, for example, a subject's neural condition. Some examples of classifiers include k-nearest neighbor ("KNN"), neural networks, and support vector machines ("SVM"). Each classifier 106, 107 may provide a variety of output results, such as a logical result or a weighted result. The classifiers 106, 107 may be customized for the individual subject and may be adapted to use only a subset of the characteristics that are most useful for the specific subject. For example, the classifier may detect pre-onset characteristics of a neurological event. Additionally, over time, the classifiers 106, 107 may be further adapted to the subject, based, for example, in part on the result of previous analyses and may reselect extracted characteristics that are used for the specific subject.

As it relates to epilepsy, for example, one implementation of a classification of neural conditions defined by the classifiers 106, 107 may include (1) an inter-ictal condition (sometimes referred to as a "normal" condition), (2) a pre-ictal condition (sometimes referred to as an "abnormal" or "pre-seizure" condition), (3) an ictal condition (sometimes referred to as a "seizure" condition), and (4) a post-ictal condition (sometimes referred to as a "post-seizure" condition). In another embodiment, it may be desirable to have the classifier classify the subject as being in one of two conditions—a pre-ictal condition or inter-ictal condition—which could correspond, respectively, to either an elevated or high propensity for a future seizure or a low propensity for a future seizure.

As noted above, instead of providing a logical answer, it may be desirable for a classifier 106, 107 to provide a weighted answer so as to further delineate within the pre-ictal condition to further allow the system to provide a more specific output communication for the subject. For example, instead of a simple logical answer (e.g., pre-ictal or inter-ictal) it may be desirable to provide a weighted output or other output that quantifies the subject's propensity, probability, likelihood and/or risk of a future neurological event using some predetermined scale (e.g., scale of 1-10, with a "1" meaning "normal" and a "10" meaning a neurological event is imminent). For example, if it is determined that the subject has an increased propensity for a neurological event (e.g., subject has entered the pre-ictal condition), but the neurological event is likely to occur on a long time horizon, the output signal could be weighted to be reflective of the long time horizon, e.g., an output of "5". However, if the output indicates that the subject is pre-ictal and it is predicted that the neurological event is imminent within the next 10 minutes, the output could be weighted to be reflective of the shorter time horizon to the neurological event, e.g., an output of "9." On the other hand, if the subject is normal, the system may provide an output of "1".

Figure 2:
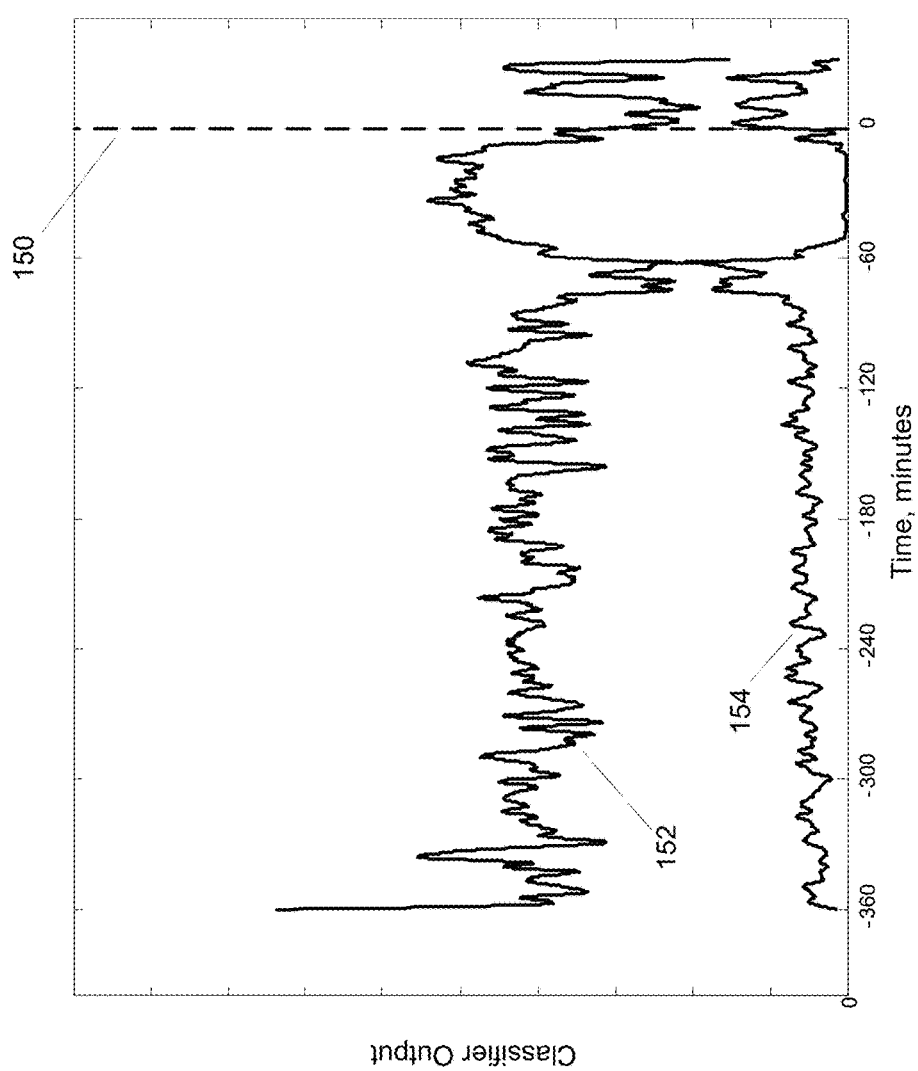
FIG. 2 is an example of a classifier output.

Other implementations involve classifier 106 outputs expressing the inter-ictal and pre-ictal conditions as a continuum, with a scalar or vector of parameters describing the actual condition and its variations. FIG. 2 depicts an example of a graphical display of the output of one embodiment of a classifier over a period of time. The output of the classifier at any point in time is a vector of two estimated probabilities: an estimated probability 152 that the input data is indicative of an inter-ictal condition and an estimated probability 154 that the input data is indicative of a pre-ictal condition. The sum of the two probabilities 152, 154, at any given time is one. The estimated probabilities 152, 154 are plotted over a period of time beginning approximately 360 minutes before the onset of a neurological event at time zero, indicated by the vertical axis 150. In the example graph, the estimated probability 152 that the data is indicative of an inter-ictal state was larger than the estimated probability 154 that the data was indicative of a pre-ictal state, until approximately 80 minutes before the onset 150 of the neurological event. The estimated probability 152 then dropped to very small values beginning approximately 50 minutes before the onset 150. The estimated probability 154 that the data is indicative of a pre-ictal state remained low until approximately 80 minutes before the onset 150 of the neurological event at which time it began to trend upward rapidly.

As described above, the computational demands of the processing provided by feature extractors 104a, 104b, 105 and classification provided by classifiers 106, 107 can be extensive. In the case of ambulatory systems supplied by portable power sources, such as implanted batteries, supplying the energy required to meet the computational demands can severely limit power source life. In some applications, physiological signals may be measured and analyzed continuously or often over long periods of time and the need to conserve energy may be particularly acute.

Figure 3:
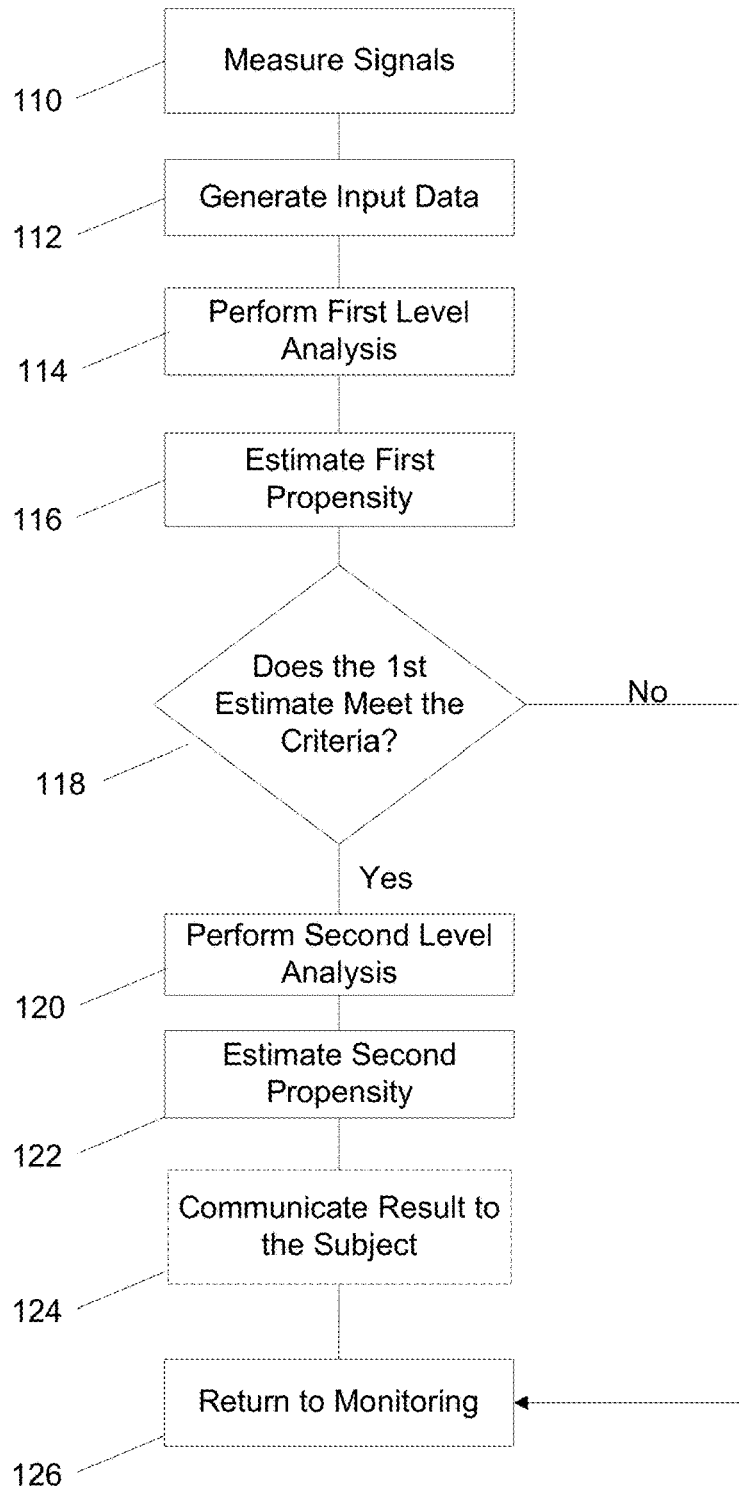
FIG. 3 is a flow chart of an embodiment of contingent analysis.

FIG. 3 depicts a simplified block diagram of a method of operating medical devices for analyzing signals that provides energy savings by enabling different parts of an overall algorithm to process signals only as needed in order to reduce energy consumption and optimize system performance. One or more physiological signals from a subject are measured 110. In one embodiment, sixteen channels of physiological signals are measured. More or fewer channels may be measured according to the particular kinds of analyses being employed. The measured signals may be pre-processed, such as, for example, by amplification, filtering, and/or conversion from analog to digital, to generate input data 112 for the analysis. Input data 112 may also comprise other subject dependent parameters (such as subject inputs and/or subject history data) that may be indicative and/or predictive of a subject's propensity for a neurological event.

Typically, the physiological signal(s) from the subject are measured during a sliding observation window or epoch. Characteristics of the sliding window may be adapted based on previous measurements and analysis. In particular, the sliding windows may operate continuously, periodically during specified intervals, or during an adaptively modified schedule (for example, to customize it to the specific subject's cycles). In some embodiments, adaptations to the sliding window can be made automatically by the system. In some embodiments, adaptations to the window may be made by a clinician. For example, if it is known that the subject is prone to have a neurological event in the morning, a clinician may program the system to continuously monitor the subject during the morning hours, while only periodically monitoring the subject during the remainder of the day. As another example, it may be less desirable to monitor a subject and provide an output to a subject when the subject is asleep. In such cases, the system may be programmed to discontinue monitoring or change the monitoring and communication protocol with the subject during a specified "sleep time" or whenever a subject inputs into the system that the subject is asleep or when the system determines that the subject is asleep. This could include intermittent monitoring, monitoring with a varying duty cycle, decreasing of the sampling frequency, or other energy saving or data minimization strategy during a time period in which the risk for a neurological event is low. Additionally, the system could enter into a low risk mode for a time period following each medication dose.

Input data 112 is subjected to a first stage analysis 114. The first stage analysis 114 may be performed by logic embodied in, for example, computer-executable instructions, such as program modules, executed by one or more computers or other devices. Generally, program modules include routines, programs, objects, components, data structures, and the like that perform particular tasks or implement particular abstract data types. Typically the functionality of the program modules may be combined or distributed as desired in various embodiments. The first stage analysis 114 may comprise the application of one or more feature extractors and a classifier such as described above. Typically, the first stage analysis 114 will comprise the application of a subset of available feature extractors applied to the input data to identify some characteristics of the signals. Preferably, the first stage analysis will be relatively low in computational demands and will have a relatively high sensitivity, but not necessarily a high specificity. In general terms, the sensitivity of the analysis is related to the probability that analysis indicates the presence of a condition given that the condition actually exists. In general terms, the specificity of the analysis is related to the probability that the analysis indicates the absence of a condition given that the condition is actually absent. The detection of particular frequencies in EEG signals is one example of feature extractor having a relatively low computational demand. The output(s) from the first set of feature extractors may be combined using a first classifier.

Based on the first stage analysis 114, a first estimate of a susceptibility or propensity for the subject to have a neurological event is determined 116. The first estimate may take the form of a qualitative characterization or may be represented quantitatively or by a combination of qualitative and quantitative characterizations. A qualitative characterization may, for example, relate to the presence of pre-onset characteristics for a neurological event. A quantitative characterization may be a single number, such as, for example, by a probability of a neurological event occurring in a predetermined time period following the measurement of the signals or an estimated time horizon during which an estimated propensity for the subject to have a neurological event is below a predetermined threshold, or a collection of values that characterize the analysis.

The first estimate 116 is then examined 118 to determine whether it meets one or more specified criteria. The specified criteria may be universal or may be adapted to a particular subject. By way of examples, the criteria may include the presence or absence of certain features in the signals or the exceedance of a threshold probability. The criteria may be modified over time. The criteria may be adapted in response to various conditions of the subject such as, for example, the subject's state of wakefulness or current activity level. The criteria may also adapted in response to current conditions of the medical device such as, for example, the current charge state of a battery.

If the criteria are not met, a second stage of analysis 120 is not performed and the system may return to a monitoring condition 126. In this instance, the computational and energy costs of the second stage analysis 120 are not incurred. For additional energy savings, for example if it is determined that a seizure is very unlikely, the system may also reduce the sampling rate or cease monitoring and turn off or go to sleep for some specified amount of time. Such embodiments will depend on the predictive value of collecting continuous monitoring data. For example, if it can be determined that the value of such data is low, turning off may be a viable option for some amount of time.

If the criteria in step 118 are met, for example if the estimate derived from the first analysis indicates an increased susceptibility or propensity for the monitored condition to exist or occur (for example, prediction of the pre-ictal condition), then the algorithm may transition from the base mode to a second or advanced mode wherein a second stage analysis 120 is performed to determine a second estimate of a propensity for the subject to have a neurological event 122. The second stage analysis 120 may be performed by logic embodied in, for example, computer-executable instructions, such as program modules, executed by one or more computers or other devices.

Depending on the particular embodiment, the set of feature extractors employed in the second stage analysis 120 may be used in conjunction with the set of feature extractors employed in the first stage analysis 114 or as an alternative to the first set of feature extractors. The set of feature extractors employed in the second stage analysis 120 will typically afford a higher level of computational complexity and/or may have a higher specificity and/or sensitivity than the set of feature extractors employed in the first stage analysis 114. In one embodiment, the second stage analysis 120 may perform more refined versions of the analyses performed by the first stage analysis 114. In another embodiment, the second stage analysis 120 may perform different kinds of analyses. In yet other embodiments, the feature extractors in the first stage analysis and second stage analysis may have multi-resolution predictions and may provide for divergent spatial predictions. For example, the first stage analysis may include feature extractors that more accurately predict over a long time horizon, while the second stage analysis may more accurately predict over a short time horizon.

The output from the second set of feature extractors may be combined in the classifier used in the first stage analysis 114 or a second classifier. The result from either classifier may, in one embodiment, have both an improved sensitivity and specificity, relative to the sensitivity and specificity of the classification based on only the first set of feature extractors. The second estimate 122 is preferably more refined than the first estimate 116 and may take the form of a qualitative or a quantitative characterization or a combination thereof It will be appreciated, however, that battery life is saved regardless of whether more or less computation is required to produce the second estimate 122 than the first estimate 116.

Once the subject's susceptibility or propensity for seizure is estimated by the predictive algorithm, a signal that is indicative of the propensity for the future seizure may optionally be communicated to the subject 124. In some embodiments, the predictive algorithm provides an output that indicates when the subject has an elevated propensity for seizure. In such embodiments, the communication output to the subject may simply be a warning or a recommendation to the subject that was programmed into the system by the clinician. In other embodiments, the predictive algorithm may output a graded propensity assessment, a quantitative assessment of the subject's condition, a time horizon until the predicted seizure will occur, or some combination thereof. In such embodiments, the communication output to the subject may provide a recommendation or instruction that is a function of the risk assessment, probability, or time horizon.

It will be recognized by those skilled in the art that the method described herein can readily be extended to encompass more than two stages of analysis. In one embodiment, the result of the first stage analysis may determine which of a plurality of second stage algorithms is selected to run. In another embodiment, the result of a second stage analysis may be used to decide whether a third stage of analysis is run, which result may trigger a fourth stage analysis, and so on.

In alternative embodiments of the energy saving methods disclosed herein, the predictive algorithms are run less often when previous results indicate that it is unlikely that a neurological event is imminent. For example, if the result of a previous execution of the algorithm indicates that it is relatively more likely that a neurological event will occur within a given time interval, the predictive algorithm may be scheduled to execute more frequently. Such variable scheduling techniques may be usefully combined with the other scheduling techniques discussed in detail herein.

Figure 4:
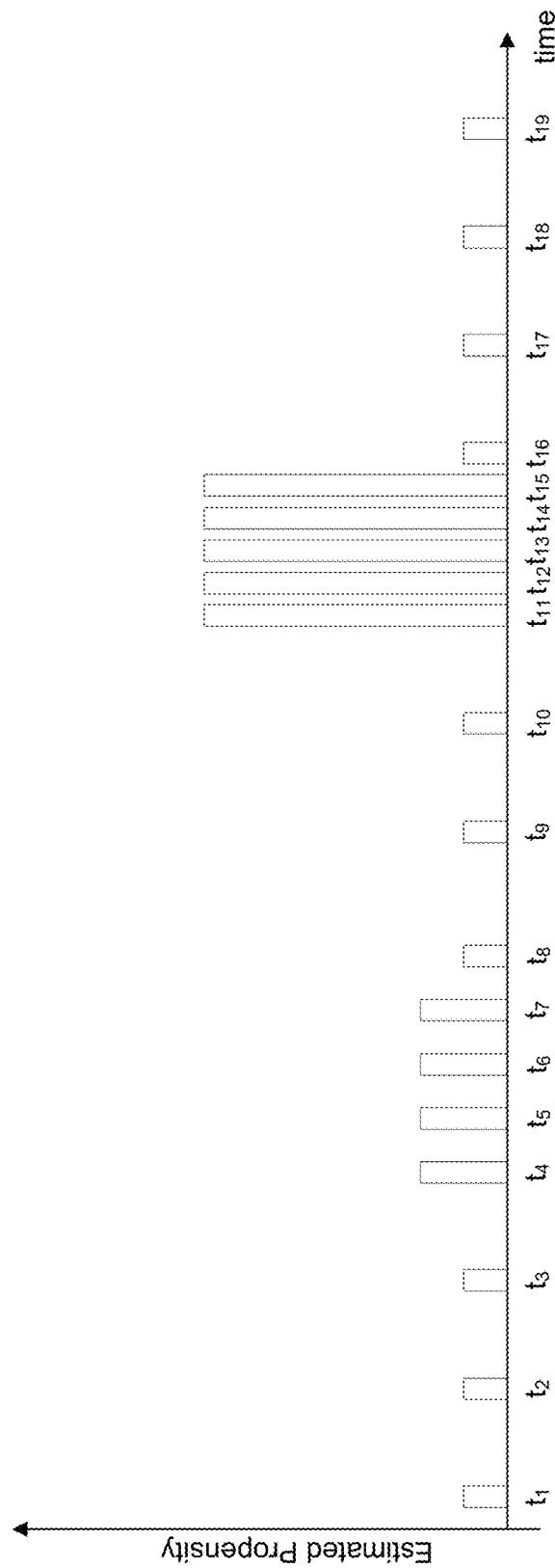
FIG. 4 is an example timeline for an embodiment of an analysis scheduling that varies temporally.

FIG. 4 depicts an illustrative example of one such alternative embodiment. Each bar represents a result of the predictive system as measuring and analysis cycles were run at various times, $t_1$, $t_2$, etc. At time $t_1$, a relatively low propensity of a neurological event was estimated and the next running of the analysis was scheduled for time $t_2$. A similarly low propensity was estimated at time $t_2$, and so the system was scheduled to be run again at time $t_3$, where the time interval $t_3$-$t_2$ is the same as the time interval $t_2$-$t_1$. At time $t_4$, an elevated propensity was estimated and so the analysis system was scheduled to execute more frequently, with a shorter interval between succeeding executions. The estimated propensity did not change again until the system was executed at time $t_8$, at which time the estimated propensity was once again lower and so the system was scheduled to run on the baseline schedule as it had been at $t_1$. At $t_{11}$, a highly elevated propensity was estimated, and so the system was scheduled to run on a much more frequent schedule which continued until a lowered propensity was estimated at time $t_{16}$.

The length and frequency of measurement and analysis cycles may be tailored to the prediction horizon. As an example, if the predictive system indicates that it is unlikely for a neurological event to occur in the next hour, the system could be scheduled to run more often than once per hour, but not so often as several hundred times per hour. Preferred scheduling frequencies would be between about 2 and about 100 times the reciprocal of the system's neurological event prediction horizon. By varying the frequency of measuring and analysis cycles according to the estimated propensity, energy savings would be realized.

In an alternative embodiment, different prediction subsystems may be run depending on the results of prior calculations. For example, if the current propensity for a neurological event is remote, a corresponding exceptionally low operating power analysis subsystem would be scheduled. If the low operating power analysis subsystem indicates an elevated propensity for a neurological event, a second, more computationally demanding and more specific subsystem would be scheduled. If the output of the second subsystem indicates a propensity above a certain threshold, a third subsystem may be scheduled, and so forth. In yet another alternative embodiment, the approaches of the two preceding embodiments may be combined. The selection of subsystems and their rates of execution may depend on the results of prior analyses.

The systems described herein may be embodied as software, hardware, firmware, or combinations thereof. In some instances, it may be desirable to have first or lower stage systems operating only in hardware in order to minimize energy requirements. The systems described above may be embodied in a device external to the subject, an implanted device, or distributed between an implanted device and an external device.

Figure 5:
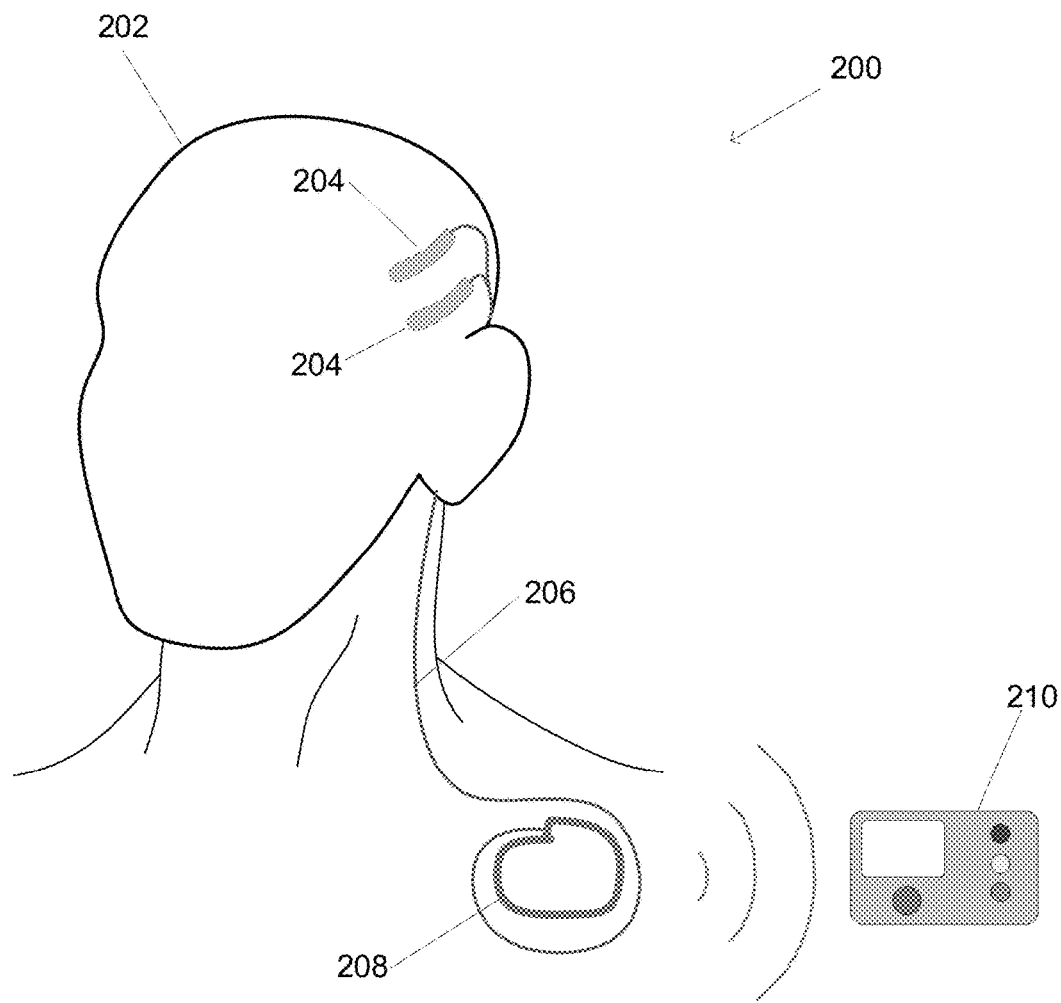
FIG. 5 is a simplified diagram of a system that embodies a contingent scheduling system.

Because the methods of the present invention are able to consume less energy than conventional algorithms and will thereby prolong the life of the power sources, the methods of the present invention will facilitate the long-term implementation of the algorithms in a portable and/or implantable device system. FIG. 5 illustrates a system in which the algorithms of the present invention may be embodied. The system 200 is used to monitor a subject 202 for purposes of detecting and predicting neurological events. The system 200 of the embodiment provides for substantially continuous sampling of brain wave electrical signals such as in electroencephalograms or electrocorticograms, referred to collectively as EEGs.

The system 200 comprises one or more sensors 204 configured to measure signals from the subject 202. The sensors 204 may be located anywhere on the subject. In the exemplary embodiment, the sensors 204 are configured to sample electrical activity from the subject's brain, such as EEG signals. The sensors 204 may be attached to the surface of the subject's body (e.g., scalp electrodes), attached to the head (e.g., subcutaneous electrodes, bone screw electrodes, and the like), or, preferably, may be implanted intracranially in the subject 202. In one embodiment, one or more of the sensors 204 will be implanted adjacent a previously identified epileptic focus, a portion of the brain where such a focus is believed to be located, or adjacent a portion of a seizure network.

Any number of sensors 204 may be employed, but the sensors 204 will preferably include between 1 sensor and 16 sensors. The sensors may take a variety of forms. In one embodiment, the sensors comprise grid electrodes, strip electrodes and/or depth electrodes which may be permanently implanted through burr holes in the head. Exact positioning of the sensors will usually depend on the desired type of measurement. In addition to measuring brain activity, other sensors (not shown) may be employed to measure other physiological signals from the subject 202.

In an embodiment, the sensors 204 will be configured to substantially continuously sample the brain activity of the groups of neurons in the immediate vicinity of the sensors 204. The sensors 204 are electrically joined via cables 206 to an implanted communication unit 208. In one embodiment, the cables 206 and communication unit 208 will be implanted in the subject 202. For example, the communication unit 208 may be implanted in a subclavicular cavity of the subject 202. In alternative embodiments, the cables 206 and communication unit 208 may be attached to the subject 202 externally.

In one embodiment, the communication unit 208 is configured to facilitate the sampling of signals from the sensors 204. Sampling of brain activity is typically carried out at a rate above about 200 Hz, and preferably between about 200 Hz and about 1000 Hz, and most preferably at about 400 Hz. The sampling rates could be higher or lower, depending on the specific conditions being monitored, the subject 202, and other factors. Each sample of the subject's brain activity is typically encoded using between about 8 bits per sample and about 32 bits per sample, and preferably about 16 bits per sample.

In alternative embodiments, the communication unit 208 may be configured to measure the signals on a non-continuous basis. In such embodiments, signals may be measured periodically or aperiodically.

An external data device 210 is preferably carried external to the body of the subject 202. The external data device 210 receives and stores signals, including measured signals and possibly other physiological signals, from the communication unit 208. External data device 210 could also receive and store extracted features, classifier outputs, patient inputs, and the like. Communication between the external data device 210 and the communication unit 208 may be carried out through wireless communication. The wireless communication link between the external data device 210 and the communication unit 208 may provide a one-way or two-way communication link for transmitting data. In alternative embodiments, it may be desirable to have a direct communications link from the external data device 210 to the communication unit 208, such as, for example, via an interface device positioned below the subject's skin. The interface (not shown) may take the form of a magnetically attached transducer that would enable power to be continuously delivered to the communication unit 208 and would provide for relatively higher rates of data transmission. Error detection and correction methods may be used to help insure the integrity of transmitted data. If desired, the wireless data signals can be encrypted prior to transmission to the external data device 210.

Figure 6:
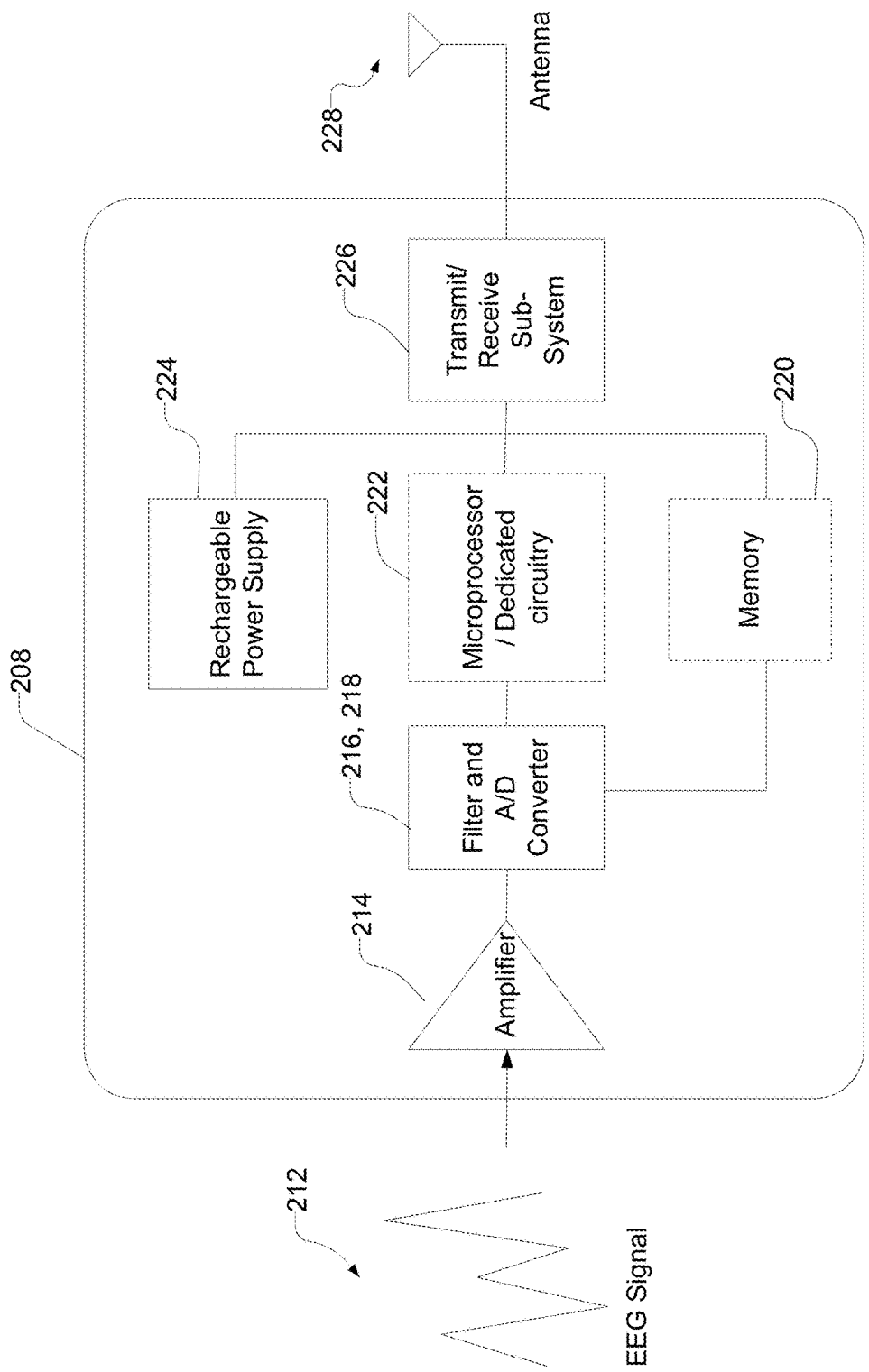
FIG. 6 is a block diagram of an implanted communications unit that may be used in accordance with the systems and methods described herein.

FIG. 6 depicts a block diagram of one embodiment of a communication unit 208 that may be used with the systems and methods described herein. Energy for the system is supplied by a rechargeable power supply 224. The rechargeable power supply may be a battery, or the like. The rechargeable power supply 224 may also be in communication with a transmit/receive subsystem 226 so as to receive power from outside the body by inductive coupling, radiofrequency (RF) coupling, and the like. Power supply 224 will generally be used to provide power to the other components of the implantable device. Signals 212 from the sensors 204 are received by the communication unit 208. The signals may be initially conditioned by an amplifier 214, a filter 216, and an analog-to-digital converter 218. A memory module 220 may be provided for storage of some of the sampled signals prior to transmission via a transmit/receive subsystem 226 and antenna 228 to the external data device 210. For example, the memory module 220 may be used as a buffer to temporarily store the conditioned signals from the sensors 204 if there are problems with transmitting data to the external data device 210, such as may occur if the external data device 210 experiences power problems or is out of range of the communications system. The external data device 210 can be configured to communicate a warning signal to the subject in the case of data transmission problems to inform the subject and allow him or her to correct the problem.

The communication unit 208 may optionally comprise circuitry of a digital or analog or combined digital/analog nature and/or a microprocessor, referred to herein collectively as "microprocessor" 222, for processing the signals prior to transmission to the external data device 210. The microprocessor 222 may execute at least portions of the analysis as described herein. For example, in some configurations, the microprocessor 222 may run one or more feature extractors 104a, 104b, 105 (FIG. 1) that extract characteristics of the measured signal that are relevant to the purpose of monitoring. Thus, if the system is being used for diagnosing or monitoring epileptic subjects, the extracted characteristics (either alone or in combination with other characteristics) may be indicative or predictive of a neurological event. Once the characteristic(s) are extracted, the microprocessor 222 may transmit the extracted characteristic(s) to the external data device 210 and/or store the extracted characteristic(s) in memory 220. Because the transmission of the extracted characteristics is likely to include less data than the measured signal itself, such a configuration will likely reduce the bandwidth requirements for the communication link between the communication unit 208 and the external data device 210.

In some configurations, the microprocessor 222 in the communication unit 208 may run one or more classifiers 106, 107 (FIG. 1) as described above with respect to FIG. 1. The result 108 (FIG. 1) of the classification may be communicated to the external data device 210.

Figure 7:
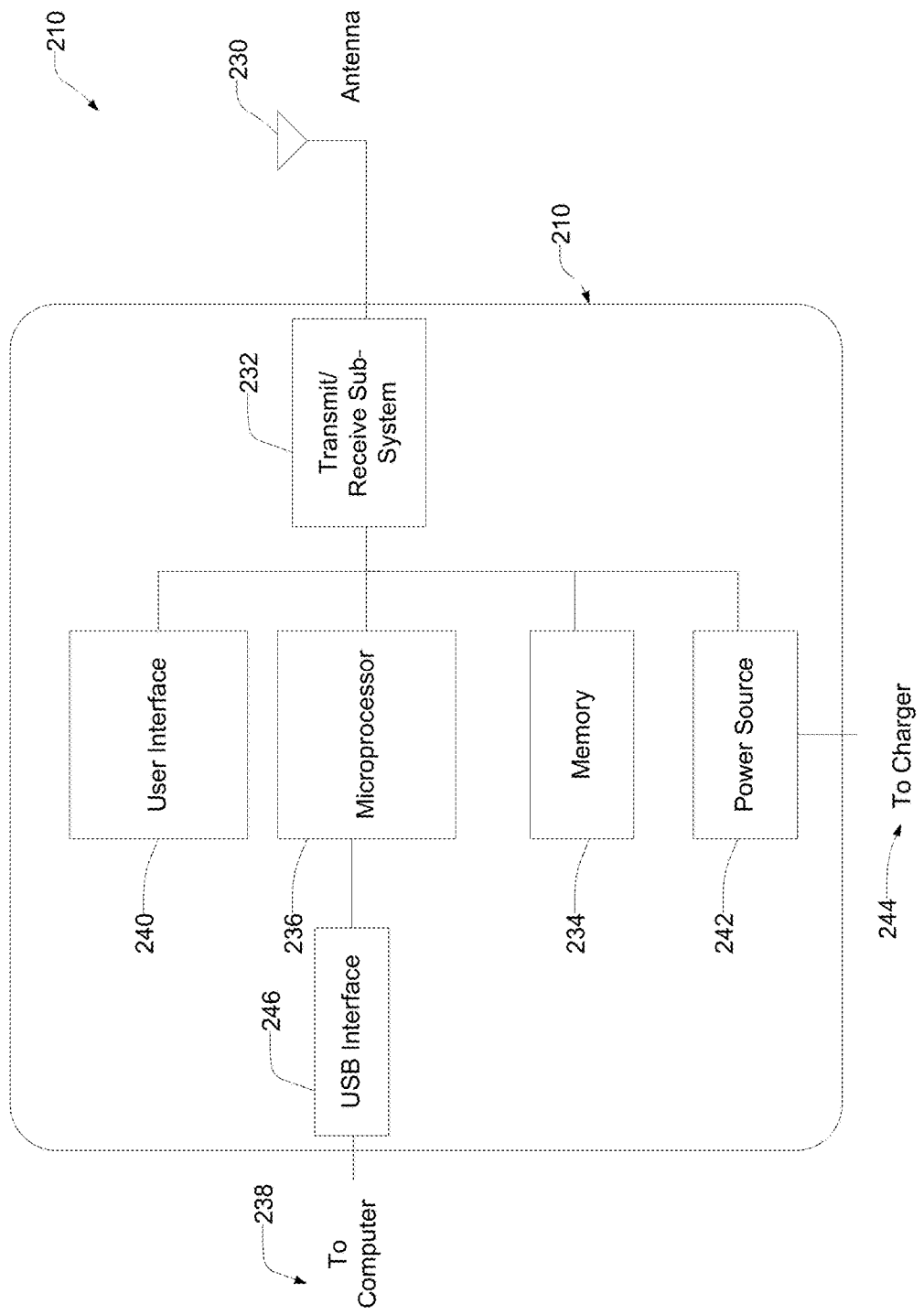
FIG. 7 is a block diagram of an external data device that may be used in accordance with the systems and methods described herein.

While the external data device 210 may include any combination of conventional components, FIG. 7 provides a schematic diagram of some of the components that may be included. Signals from the communication unit 208 are received at an antenna 230 and conveyed to a transmit/receive subsystem 232. The signals received may include, for example, a raw measured signal, a processed measured signal, extracted characteristics from the measured signal, a result from analysis software that ran on the implanted microprocessor 222, or any combination thereof.

The received data may thereafter be stored in memory 234, such as a hard drive, random access memory ("RAM"), electrically erasable programmable read-only memory ("EEPROM"), removable flash memory, or the like and/or processed by a microprocessor, application specific integrated circuit (ASIC) or other dedicated circuitry of a digital or analog or combined digital/analog nature, referred to herein collectively as a "microprocessor" 236. Microprocessor 236 may be configured to request that the communication unit 208 perform various checks (e.g., sensor impedance checks) or calibrations prior to signal recording and/or at specified times to ensure the proper functioning of the system.

Data may be transmitted from memory 234 to microprocessor 236 where the data may optionally undergo additional processing. For example, if the transmitted data is encrypted, it may be decrypted. The microprocessor 236 may also comprise one or more filters that filter out low-frequency or high-frequency artifacts (e.g., muscle movement artifacts, eye-blink artifacts, chewing, and the like) so as to prevent contamination of the measured signals.

External data device 210 will typically include a user interface 240 for displaying outputs to the subject and for receiving inputs from the subject. The user interface will typically comprise outputs such as auditory devices (e.g., speakers) visual devices (e.g., liquid-crystal display ("LCD"), light-emitting diodes ("LEDs")), tactile devices (e.g., vibratory mechanisms), or the like, and inputs, such as a plurality of buttons, a touch screen, and/or a scroll wheel.

The user interface may be adapted to allow the subject to indicate and record certain events. For example, the subject may indicate that medication has been taken, the dosage, the type of medication, meal intake, sleep, drowsiness, occurrence of an aura, occurrence of a neurological event, or the like. Such inputs may be used in conjunction with the measured data to improve the analysis.

The LCD display may be used to output a variety of different communications to the subject including, status of the device (e.g., memory capacity remaining), battery state of one or more components of system, whether or not the external data device 210 is within communication range of the communication unit 208, a warning (e.g., a neurological event warning), a prediction (e.g., a neurological event prediction), a recommendation (e.g., "take medicine"), or the like. It may be desirable to provide an audio output or vibratory output to the subject in addition to or as an alternative to the visual display on the LCD.

External data device 210 may also include a power source 242 or other conventional power supply that is in communication with at least one other component of external data device 210. The power source 242 may be rechargeable. If the power source 242 is rechargeable, the power source may optionally have an interface for communication with a charger 244. External data device 210 may also include a USB interface 246 configured to communicate with a computer 238. While not shown in FIG. 7, external data device 210 will typically comprise a clock circuit (e.g., oscillator and frequency synthesizer) to provide the time base for synchronizing the external data device 210 and the communication unit 208.

Referring again to FIG. 5, in a preferred embodiment, most or all of the processing of the signals received by the communication unit 208 is done in an external data device 210 that is external to the subject's body. In such embodiments, the communication unit 208 would receive the signals from subject and may or may not pre-process the signals and transmit some or all of the measured signals transcutaneously to an external data device 210, where the prediction of the neurological event and possible therapy determination is made. Advantageously, such embodiments reduce the amount of computational processing power that needs to be implanted in the subject, thus potentially reducing energy consumption and increasing battery life. Furthermore, by having the processing external to the subject, the judgment or decision making components of the system may be more easily reprogrammed or custom tailored to the subject without having to reprogram the communication unit 208.

In alternative embodiments, the predictive systems disclosed herein and treatment systems responsive to the predictive systems may be embodied in a device that is implanted in the subject's body, external to the subject's body, or a combination thereof. For example, in one embodiment the predictive system may be stored in and processed by the communication unit 208 that is implanted in the subject's body. A treatment analysis system, in contrast, may be processed in a processor that is embodied in an external data device 210 external to the subject's body. In such embodiments, the subject's propensity for neurological event characterization (or whatever output is generated by the predictive system that is predictive of the onset of the neurological event) is transmitted to the external subject communication assembly, and the external processor performs any remaining processing to generate and display the output from the predictive system and communicate this to the subject. Such embodiments have the benefit of sharing processing power, while reducing the communications demands on the communication unit 208. Furthermore, because the treatment system is external to the subject, updating or reprogramming the treatment system may be carried out more easily.

In other embodiments, the signals 212 may be processed in a variety of ways in the communication unit 208 before transmitting data to the external data device 210 so as to reduce the total amount of data to be transmitted, thereby reducing the power demands of the transmit/receive subsystem 226. Examples include: digitally compressing the signals before transmitting them; selecting only a subset of the measured signals for transmission; selecting a limited segment of time and transmitting signals only from that time segment; extracting salient characteristics of the signals, transmitting data representative of those characteristics rather than the signals themselves, and transmitting only the result of classification. Further processing and analysis of the transmitted data may take place in the external data device 210.

In yet other embodiments, it may be possible to perform some of the prediction in the communication unit 208 and some of the prediction in the external data device 210. For example, one or more characteristics from the one or more signals may be extracted with feature extractors in the communication unit 208. Some or all of the extracted characteristics may be transmitted to the external data device 210 where the characteristics may be classified to predict the onset of a neurological event. If desired, external data device 210 may be customizable to the individual subject. Consequently, the classifier may be adapted to allow for transmission or receipt of only the characteristics from the communication unit 208 that are predictive for that individual subject. Advantageously, by performing feature extraction in the communication unit 208 and classification in an external device at least two benefits may be realized. First, the amount of wireless data transmitted from the communication unit 208 to the external data device 210 is reduced (versus transmitting pre-processed data). Second, classification, which embodies the decision or judgment component, may be easily reprogrammed or custom tailored to the subject without having to reprogram the communication unit 208.

In yet another embodiment, feature extraction may be performed external to the body. Pre-processed signals (e.g., filtered, amplified, converted to digital) may be transcutaneously transmitted from communication unit 208 to the external data device 210 where one or more characteristics are extracted from the one or more signals with feature extractors. Some or all of the extracted characteristics may be transcutaneously transmitted back into the communication unit 208, where a second stage of processing may be performed on the characteristics, such as classifying of the characteristics (and other signals) to characterize the subject's propensity for the onset of a future neurological event. If desired, to improve bandwidth, the classifier may be adapted to allow for transmission or receipt of only the characteristics from the subject communication assembly that are predictive for that individual subject. Advantageously, because feature extractors may be computationally expensive and energy hungry, it may be desirable to have the feature extractors external to the body, where it is easier to provide more processing and larger power sources.

For additional energy savings, the systems of the present invention may also embody some of the energy saving concepts described in commonly owned, copending Patent application Ser. No. 11/616,793, entitled "Low Power Device with Variable Scheduling," filed Dec. 27, 2006, pending, the complete disclosure of which is incorporated herein by reference.

More complete descriptions of systems that may embody the concepts of the present invention are described in commonly owned U.S. Pat. No. 8,868,172, filed Dec. 28, 2005, U.S. Pat. No. 8,725,243, filed Dec. 28, 2005, and U.S. patent application Ser. No. 11/322,150, filed on Dec. 28, 2005, published as US 2007/0149952 A1, abandoned, the complete disclosures of which are incorporated herein by reference.

The inventive aspects described herein may be applicable to commercial monitoring systems. For example, the systems herein may be applied to the NeuroPace® RNS system. Such commercial systems extract half-wave amplitude and duration, sum of absolute differences as an approximation of signal curve length (which is in turn a simplification of waveform fractal dimension), and a modified sum of absolute amplitudes as an approximation of signal energy. Instead of running all of the feature extractors continuously all of the time, subsequent measurement and analysis cycles may be scheduled based on analysis of previous measurement cycles. In some embodiments, the measuring and analysis cycles are run less often when the previous measurements indicates that it is relatively unlikely that a seizure is imminent. On the other hand, if previous measurements indicate that a seizure is relatively likely to be proximate, the measurement and analysis cycles are run more frequently, up to, possibly, some predetermined maximum rate. Such a feature extractor configuration will preserve computation power, reduce battery usage, and prolong the time between battery changes.

Figure 8:
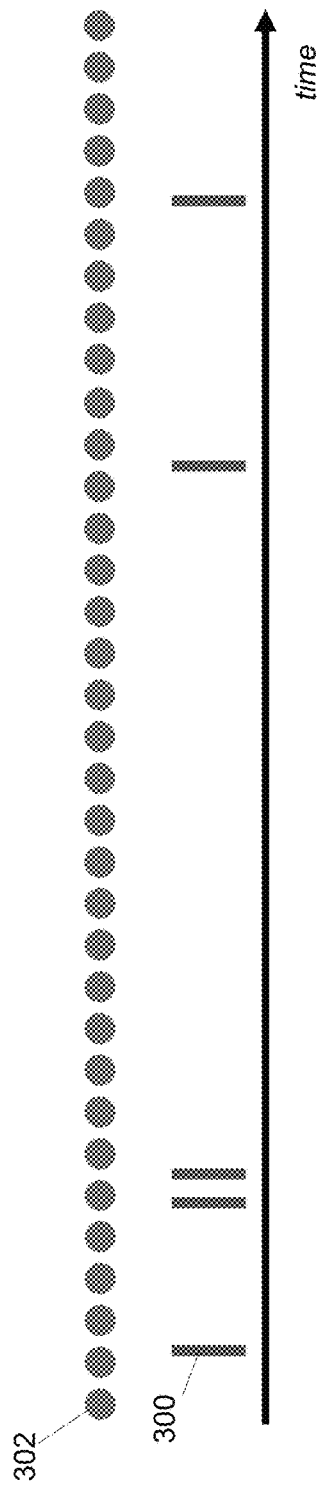
FIG. 8 is an example timeline for a typical therapeutic regimen for the treatment of epilepsy.

The ability to provide long-term low-power ambulatory measuring of physiological signals and prediction of neurological events can facilitate improved treatment regimens for certain neurological conditions. FIG. 8 depicts the typical course of treatment for a subject with epilepsy. Because the occurrence of neurological events 300 over time has been unpredictable, present medical therapy relies on continuous prophylactic administration of anti-epileptic drugs ("AEDs"). Constant doses 302 of one or more AEDs are administered to a subject at regular time intervals with the objective of maintaining relatively stable levels of the AEDs within the subject. Maximum doses of the AEDs are limited by the side effects of their chronic administration.

Figure 9:
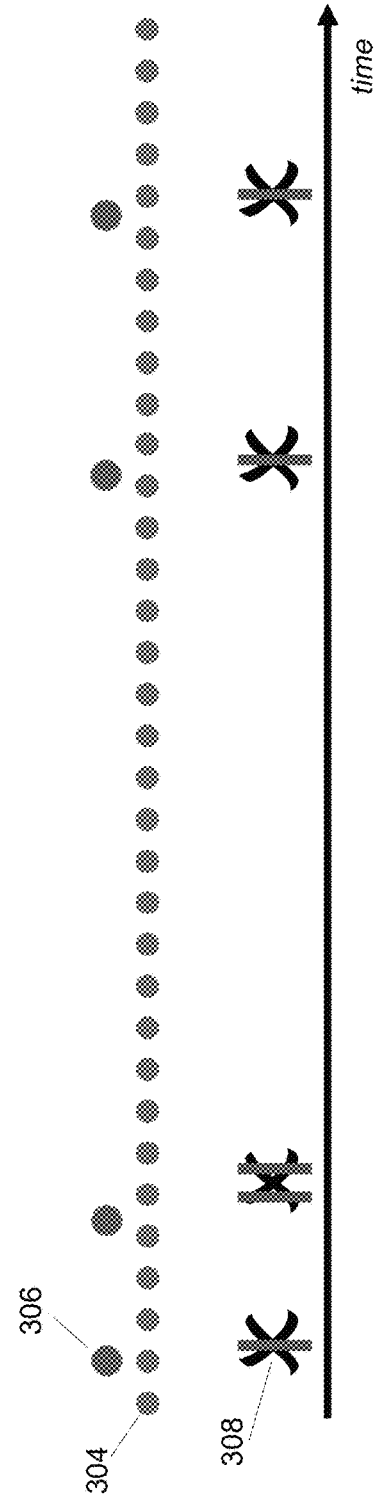
FIG. 9 is an example timeline for a therapeutic regimen for the treatment of epilepsy that may be enabled by the system and methods described herein.

Reliable long-term essentially continuously operating neurological event prediction systems would facilitate epilepsy treatment. Therapeutic actions, such as, for example, brain stimulation, peripheral nerve stimulation (e.g., vagus nerve stimulation), cranial nerve stimulation (e.g., trigeminal nerve stimulation ("TNS")), or targeted administration of AEDs, could be directed by output from a neurological event prediction system. One such course of treatment is depicted in FIG. 9. Relatively lower constant doses 304 of one or more AEDs may be administered to a subject at regular time intervals in addition to or as an alternative to the prophylactic administration of AEDs. Supplementary medication doses 306 are administered just prior to an imminent neurological event 308. By targeting the supplementary doses 306 at the appropriate times, neurological events may be more effectively controlled and potentially eliminated 308, while reducing side effects attendant with the chronic administration of higher levels of the AEDs.

While the present disclosure has been described in connection with various embodiments, illustrated in the various figures, it is understood that similar aspects may be used or modifications and additions may be made to the described aspects of the disclosed embodiments for performing the same function of the present disclosure without deviating therefrom. Other equivalent mechanisms to the described aspects are also contemplated by the teachings herein. Therefore, the present disclosure should not be limited to any single aspect, but rather construed in breadth and scope in accordance with the appended claims.

What is claimed:

1. A method of operating a medical device configured to monitor a subject, the method comprising:
  receiving, at a processor set in a base mode, a first signal reflective of neurological activity of the subject from a sensor communicating with the subject;
  performing a first analysis of the first signal to estimate a first propensity for the subject to have a neurological event, including analyzing the first signal by a first set of feature extractors, in response to receiving the first signal;
  computationally determining that the first propensity meets one or more specified criteria;
  transitioning the processor from the base mode to an advanced mode in response to the first propensity meeting the one or more specified criteria;
  receiving, at the processor, a second signal reflective of neurological activity of the subject subsequent in time to the first signal in response to transitioning the processor from the base mode to the advanced mode; and
  performing a second analysis of the second signal to estimate a second propensity for the subject to have the neurological event, including analyzing the second signal by a second set of feature extractors different from the first set of feature extractors, the first analysis requiring less computational power than the second analysis, in response to receiving the second signal.

2. The method of claim 1 wherein receiving the first signal comprises measuring, by the sensor, one or more electrical signals generated by neural activity.

3. The method of claim 1 wherein the first set of feature extractors comprises one or more feature extractors selected from the group consisting of frequency based feature extractors, phase coherence feature extractors, and band power feature extractors.

4. The method of claim 1 wherein at least one of the one or more specified criteria is selected based on information about the subject.

5. The method of claim 1 wherein said second set of feature extractors is characterized by higher specificity and higher computational complexity than the first set of feature extractors.

6. The method of claim 1 wherein said second set of feature extractors has a higher computational demand than the first set of feature extractors.

7. The method of claim 1 wherein performing the first analysis comprises estimating a probability for the subject to have the neurological event within a specified time frame.

8. The method of claim 1 wherein at least one of the first propensity or the second propensity is a seizure status.

9. The method of claim 1 further comprising:
communicating to a care provider information indicative of the second propensity.

10. The method of claim 1 further comprising:
communicating to a care giver information regarding the second propensity.

11. The method of claim 10 wherein said communicating comprises communicating via a user interface of an external battery-powered device.

12. The method of claim 1 wherein receiving the first signal comprises receiving one or more electrical signals generated by neural activity using electrodes coupled to the subject's head.

13. The method of claim 1 wherein said sensor comprises a physiological sensor configured to gather signals reflective of neurological activity of the subject.

14. The method of claim 13 wherein the first signal comprises at least one neurological signal.

15. The method of claim 14 wherein said at least one neurological signal comprises at least one electroencephalogram (EEG) signal.

16. The method of claim 1 wherein the second signal is from the sensor communicating with the subject.

17. The method of claim 1, wherein the second signal is received from another sensor communicating with the subject.

18. The method of claim 1 wherein the second analysis involves the use of at least one additional feature extractor and/or classifier.

19. The method of claim 1 wherein the second analysis is performed repeatedly after the first analysis.

20. The method of claim 1 further comprising:
issuing an alert in response to performing the first analysis and/or the second analysis.

21. A method of processing signals received from a subject, the method comprising:
receiving a first signal reflective of neurological activity of the subject from a sensor communicating with the subject;
using a processor configured to perform a first analysis of the first signal to estimate a first propensity for the subject to have a neurological event, including analyzing the first signal with a first set of feature extractors, in response to receiving the first signal;
determining that the first propensity meets one or more specified criteria; and
in response to determining that the first propensity meets the one or more specified criteria, using the processor to perform a second analysis of a second signal reflective of neurological activity of the subject subsequent in time to the first signal to estimate a second propensity for the subject to have the neurological event, including analyzing the second signal by a second set of feature extractors different from the first set of feature extractors, wherein the first analysis requires less processor power than the second analysis.

* * * * *